United States Patent [19]
Erdman et al.

[11] Patent Number: 5,184,306
[45] Date of Patent: Feb. 2, 1993

[54] AUTOMATED HIGH-PRECISION FABRICATION OF OBJECTS OF COMPLEX AND UNIQUE GEOMETRY

[75] Inventors: Arthur G. Erdman, New Brighton; Elizabeth D. Rekow, Fridley; Donald R. Riley, Edina; Barney Klamecki, Minneapolis; Yang Zhu, St. Paul, all of Minn.; Jeong-Ho Ahn, Seoul, Rep. of Korea

[73] Assignee: Regents of the University of Minnesota, Minneapolis, Minn.

[21] Appl. No.: 812,588

[22] Filed: Dec. 20, 1991

Related U.S. Application Data

[63] Continuation of Ser. No. 365,140, Jun. 9, 1989, Pat. No. 5,128,870.

[51] Int. Cl.$^5$ .................. G06F 15/46; G06F 15/60
[52] U.S. Cl. .................. 364/474.05; 364/474.2; 364/474.24; 364/413.28; 395/119; 395/137; 395/139; 395/161
[58] Field of Search ............. 364/474.05, 474.06, 364/474.18, 474.2, 474.29, 468, 413.13, 413.16, 413.28; 382/1, 6, 9, 46; 433/55, 68, 73, 204, 213, 214, 223; 425/2; 340/705, 724, 727, 734; 395/119, 120, 125, 133, 134, 139, 161

[56] References Cited

U.S. PATENT DOCUMENTS

| Re. 25,930 | 12/1965 | Agnew | 156/58 |
|---|---|---|---|
| 3,338,766 | 8/1967 | Agnew | 156/58 |
| 3,861,044 | 1/1975 | Swinson, Jr. | 433/218 |
| 4,158,325 | 6/1979 | Dixon | 409/115 |
| 4,324,546 | 4/1982 | Heitlinger et al. | 433/25 |
| 4,485,409 | 11/1984 | Schumacher | 358/294 |
| 4,575,805 | 3/1986 | Moermann et al. | 364/474.05 |
| 4,657,394 | 4/1987 | Halioua | 356/376 |
| 4,661,289 | 4/1987 | Duret et al. | 364/474.24 |
| 4,663,720 | 5/1987 | Duret et al. | 364/474.24 |

(List continued on next page.)

FOREIGN PATENT DOCUMENTS

| 1264919 | 4/1988 | European Pat. Off. |
|---|---|---|
| 0342238 | 11/1989 | European Pat. Off. |
| 0348247 | 12/1989 | European Pat. Off. |
| 2950847 | 12/1979 | Fed. Rep. of Germany |
| 2517052 | 5/1983 | France |
| 2536654 | 6/1984 | France |

OTHER PUBLICATIONS

Rekow, Erdman & Speidel, *A Review of Development In Computer-Based Systems to Image Teeth and Produce Dental Restorations* Nov. 1987; p. 568.

Rekow, *Computer-Aided Design and Manufacturing In*

(List continued on next page.)

Primary Examiner—Joseph Ruggiero
Attorney, Agent, or Firm—Merchant, Gould, Smith, Edell, Welter and Schmidt

[57] ABSTRACT

The present invention provides a method and apparatus for the automated reproduction of three dimensional objects of complex and unique geometry. A computer acquires data describing an object and its surroundings, constructs a computer-based three dimensional model of the object from that data, superimposes an ideal geometry on the computer-based model, alters the ideal geometry to fit the form and function required of the reproduction, and then guides a milling machine in the fabrication of the reproduction. In contrast to the prior art, the present invention does not require human intervention in the reproduction process. The present invention provides two preferred embodiments for the automated high precison reproduction of objects of complex and unique geometry. Both embodiments can machine reproductions solely from generic forms stored in the computer, thus eliminating the need for scanning. Alternatively, the reproductions may be machined solely from scanned data, without resort to generic forms stored in the computer.

52 Claims, 20 Drawing Sheets

U.S. PATENT DOCUMENTS

| | | | |
|---|---|---|---|
| 4,697,347 | 10/1987 | Goudswaard | 33/1 A |
| 4,705,401 | 11/1987 | Addleman et al. | 356/376 |
| 4,725,730 | 2/1988 | Kato et al. | 250/307 |
| 4,734,034 | 3/1988 | Maness et al. | 433/68 |
| 4,742,464 | 5/1988 | Duret et al. | 364/474.24 |
| 4,752,964 | 6/1988 | Okada et al. | 364/474.05 |
| 4,766,704 | 8/1988 | Brandestini et al. | 364/413.28 |
| 4,821,200 | 4/1989 | Oberg | 364/474.24 |
| 4,837,703 | 6/1989 | Kakazu et al. | 364/474.24 |
| 4,837,732 | 6/1989 | Brandestini et al. | 364/413.28 |
| 4,846,577 | 7/1989 | Grindon | 356/376 |
| 4,901,253 | 2/1990 | Iwano et al. | 395/119 |
| 4,918,611 | 4/1990 | Shyu et al. | 364/474.08 |
| 4,936,862 | 6/1990 | Walker et al. | 364/468 |
| 4,956,787 | 9/1990 | Ito et al. | 364/474.24 |

OTHER PUBLICATONS

*Dentistry: A Review of the State of the Art*; Oct. 1987; p. 514.

D. H. Ballard & C. M. Brown, *Computer Vision*; 1982; pp. 239–243, 473.

D. F. Rogers and J. A. Adams, *Mathematical Elements For Computer Graphics*; 1976; pp. 5, 144–155, 157–187.

P. Lancaster and K. Salkauskas, *Curve & Surface Fitting*; 1986; pp. 87–112 and pp. 245–271.

S. Peterson, X. Zhu and D. Riley, *A New Algorithm for Constructing B-Spline Surfaces*; 1984; pp. 137–144.

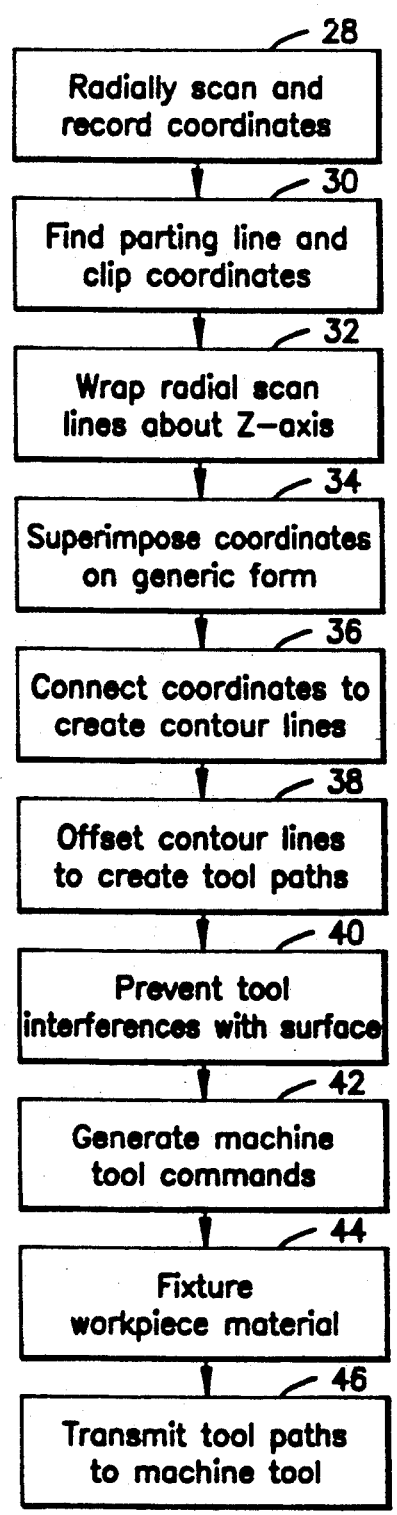
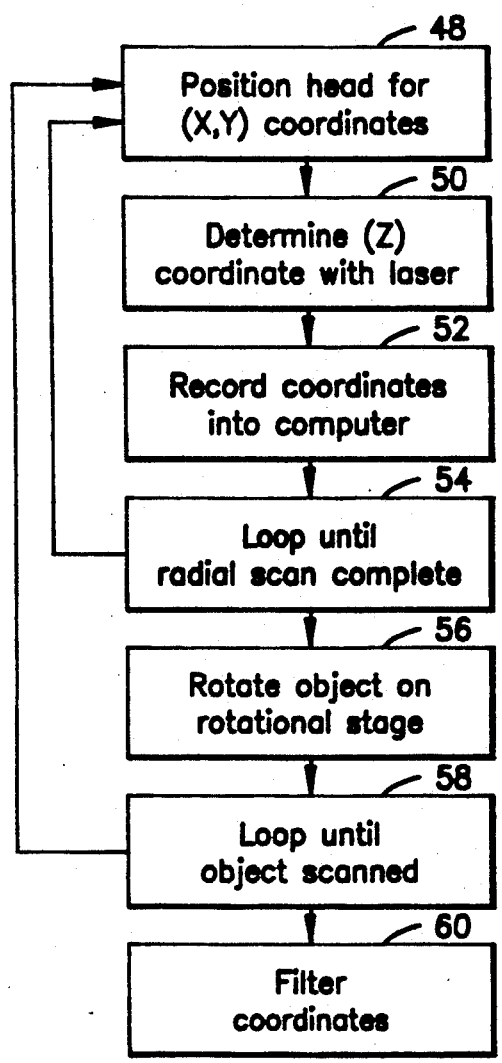
FIRST EMBODIMENT
(SYSTEM DESCRIPTION)
FIRST EMBODIMENT
(DATA ACQUISITION)
FIG. 2
FIG. 3

FIRST EMBODIMENT
(PARTING LINE METHOD)

FIRST EMBODIMENT
(SCALING METHOD)

FIRST EMBODIMENT
(SUPERPOSITION METHOD)

FIRST EMBODIMENT
(FEATURE EMPHASIS METHOD)

FIG. 6
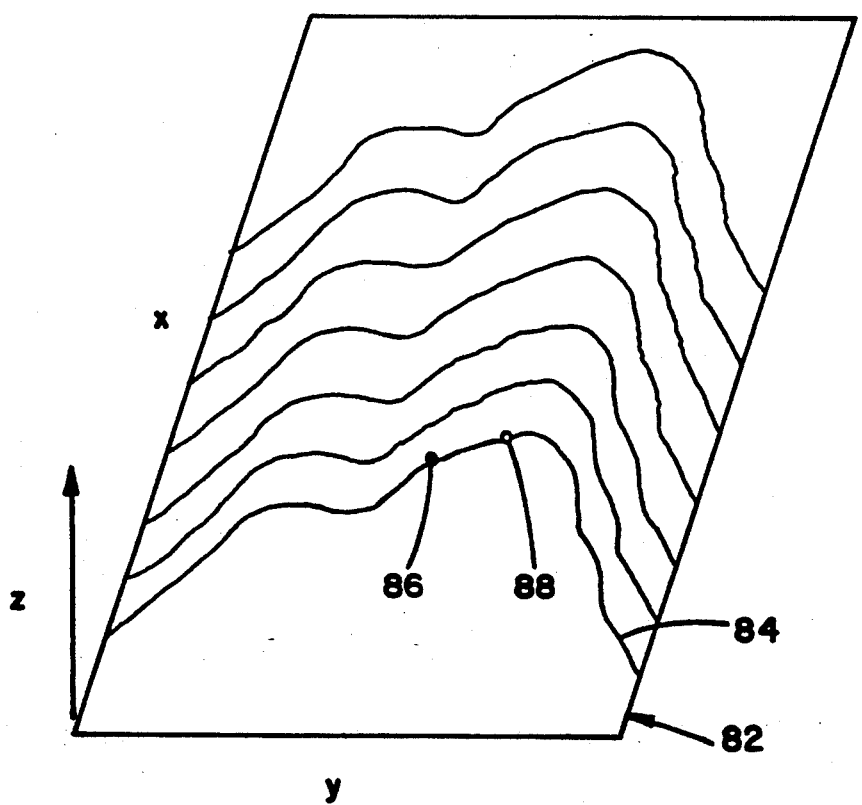
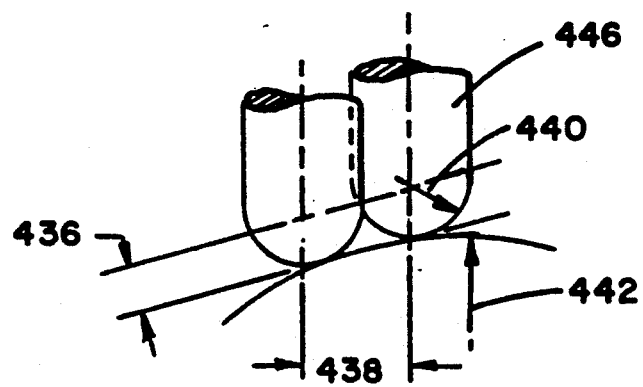
FIG. 39

FIRST EMBODIMENT
(SHAPING OF GENERIC FORM)

FIRST EMBODIMENT
(CONTOURING METHOD)

FIRST EMBODIMENT
(OFFSET TOOL PATHS)

FIG. 22
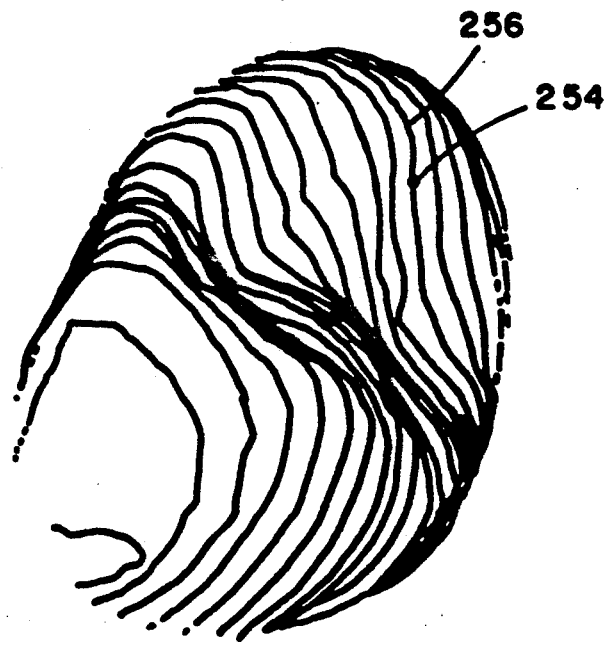
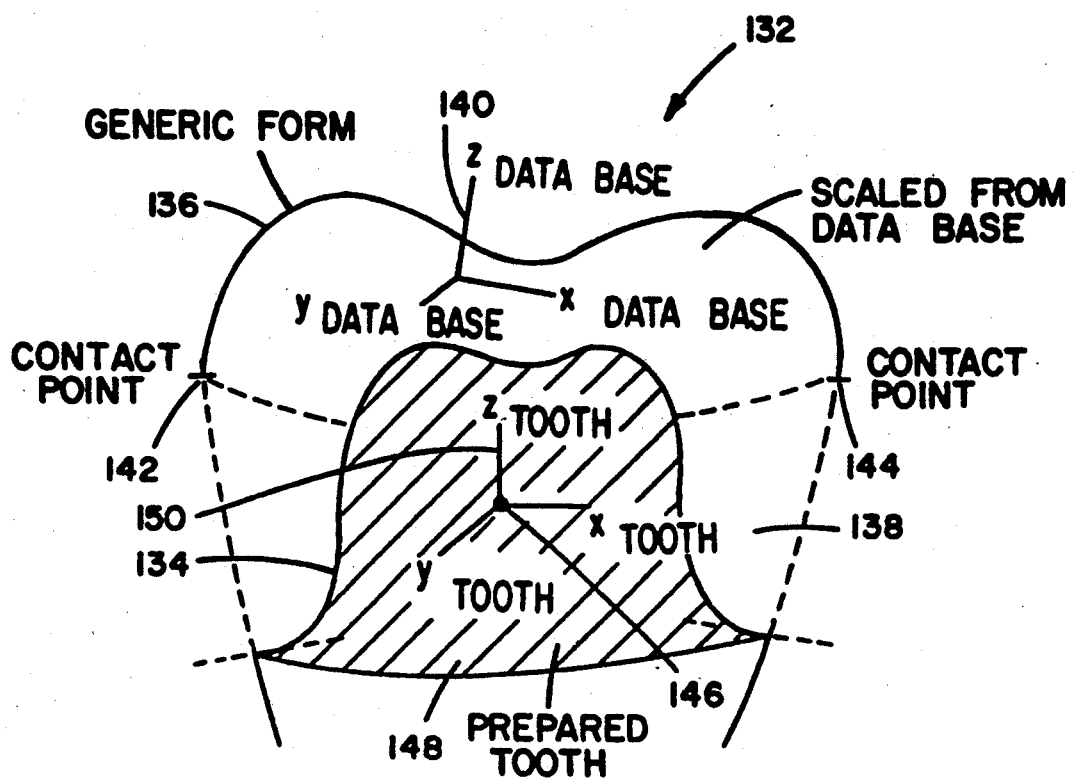
FIG. 12

FIRST EMBODIMENT
(TOOL INTERFERENCE)

SECOND EMBODIMENT
(SYSTEM DESCRIPTION)

SECOND EMBODIMENT
(FIRST SCANNING METHOD)

SECOND EMBODIMENT
(SECOND SCANNING METHOD)

SECOND EMBODIMENT
(SUPERPOSITION METHOD)

SECOND EMBODIMENT
(FEATURE METHOD)

SECOND EMBODIMENT
(SCALING METHOD)

SECOND EMBODIMENT
(SURFACE PATCH
METHOD)

SECOND EMBODIMENT
(PARTING LINE METHOD)

SECOND EMBODIMENT
(SEGMENTIZED SEARCHING
CIRCLE METHOD)

MAGNIFICATION OF NORMALIZED PATCH B

SECOND EMBODIMENT (CONTOURING METHOD)

SECOND EMBODIMENT (OFFSET TOOL PATH METHOD)

BOTH EMBODIMENTS (FIXTURING METHOD)

BOTH EMBODIMENTS (MACHINING METHOD)

SECOND EMBODIMENT
(TOOL INTERFERENCE CHECK METHOD)

BOTH EMBODIMENTS
(STEP LENGTH OPTIMIZATION METHOD)

BOTH EMBODIMENTS
(CUTTER FEED RATE
OPTIMIZATION METHOD)

BOTH EMBODIMENTS
(SCALLOP HEIGHT
OPTIMIZATION METHOD)

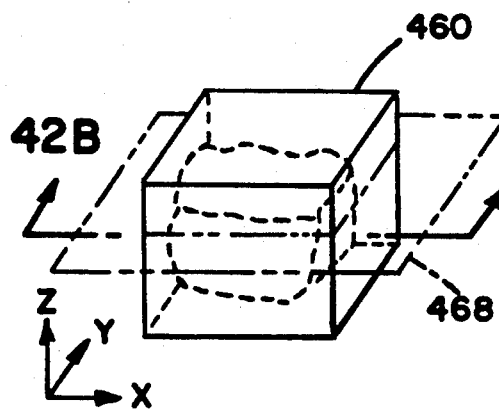
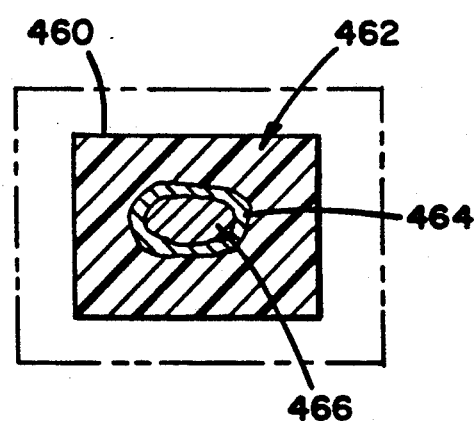
FIG. 42A  FIG. 42B
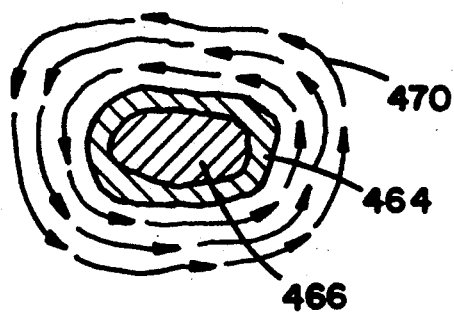
FIG. 42C
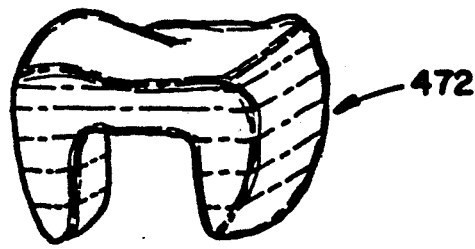
FIG. 43

AUTOMATED HIGH-PRECISION FABRICATION OF OBJECTS OF COMPLEX AND UNIQUE GEOMETRY

This invention was made with Government support under Grant Numbers 4F-32-DE 05377 and 1R-29-DE 08455 awarded by the National Institute for Dental Research. The Government has certain rights in this invention.

This is a continuation of application Ser. No. 07/365,140, filed Jun. 9, 1989, now U.S. Pat. No. 5,128,870.

TECHNICAL FIELD OF THE INVENTION

This invention relates generally to an automated system for directing the operation of machine tools. In particular, it is directed to a computerized system that machines a reproduction of a three dimensional object such that the reproduction substantially duplicates all surfaces of the object. In the context of this specification, a "reproduction" is a category of items which comprises replacement parts satisfying a particular fit and function, facsimiles generated solely from computer-based models, as well as exact or close imitations of existing objects.

BACKGROUND OF THE INVENTION

There are many applications which require the reproduction or fabrication of one-of-a-kind parts of complex geometry. These applications include dental prostheses, in-the-ear hearing aid housings, molds or implants to replace damaged bones, etc. In such applications, the replacement parts are unique. Most of the applications require a highly precise fit of the replacement part.

Dental prostheses require precise replacement parts. Traditionally, the production of dental prostheses or restorations use lost-wax casting techniques. A dentist first removes all the decay from the tooth and ensures the
integrity of the patient's remaining tooth structure. The dentist then makes an impression of the remaining tooth structure and the other teeth in the same dental arch. Usually, the dentist also makes an impression of the teeth in the opposing dental arch. The impressions are made using an elastomeric material. The elastomeric material is mixed, placed in a mouth-shaped tray for support, placed in the patient's mouth over the teeth and surrounding tissues, and held in place until it "sets." Setting times vary with the materials used, but generally range from 2 to 12 minutes per impression. When the elastomeric material sets, it has a consistency similar to that of modeling clay, but retains an elastomeric property so that it can slide past the crest of convexity of the teeth without being permanently distorted. When removed from the mouth, the elastomeric material creates a three dimensional negative of the teeth and their relative positions to each other. After the impressions are made, dental stone (plaster) is poured into the impressions and allowed to harden. The elastomeric material is then removed and discarded. Pins ar set into the bottom of the arch containing the tooth to be restored. A base of plaster is poured over the pins. When the plaster has hardened, the area of plaster supporting the model of the prepared tooth is sectioned out. The pins and the holes in a second pour of the plaster serve as guides, permitting the cast of the prepared tooth (called a die) to be removed and reinserted into the plaster cast. Excess plaster around the base of the die is removed and the position of the margin of the restoration marked. A separating medium is applied to the die. A wax pattern is then prepared directly on the die. If jaw interrelationships have been recorded, the wax pattern is mounted on an articulator. The articulator is used as a device to represent the motion of the teeth to each other. After the wax pattern is completed, it is sprued and invested for casting. When the investment material has set, the investment and pattern are placed in an oven where the wax is burned away. The remaining cavity in the investment is then filled with molten metal or other casting material. The casting is quenched and recovered. The sprue is removed and the casting is finished. Finishing operations involve removing all remaining investment material and polishing the surface. Surface polish is done by hand using an array of burrs and stones of increasingly finer grit. Final finishing is done with rouge on a soft bristle brush or rag wheel. After final finishing, the restoration is ready for the patient. The restoration is placed on the tooth and the occlusal, functional, and proximal contacts are checked. The quality of the margins is also evaluated.

The clinical criteria for acceptance include:

1. Marginal fit: A dental explorer is passed from restoration to tooth and from tooth to restoration with the tip of the explorer held perpendicular to the surfaces of both. If the interface between the restoration and tooth can be detected, the restoration should not be permanently seated but instead should be remade. Depending on the location of the margin relative to the gum tissue, a gap of 20 to 100 microns can be detected.

2. Occlusal fit: A mark should be made when the teeth tap together with a piece of occlusal marking paper placed between the teeth. The patient should not detect excessive pressure on that tooth or report any discomfort. All other teeth which contact without the restoration in place must also contact with the restoration in place.

3. Interproximal fit: A piece of dental floss should "snap" as it passes between the restoration and the adjacent contact tooth.

4. Functional fit: As the teeth move through their normal excursions, the restoration should not contact prematurely.

If the restoration can be modified to pass the acceptance criteria, it is cemented in place. If the restoration cannot pass these acceptance criteria, a new impression is made and the process begins again.

SUMMARY OF THE INVENTION

To overcome the limitations in the prior art discussed above and to overcome other limitations readily recognizable to those skilled in the art, the present invention provides a method and apparatus for the automated reproduction of three dimensional objects of complex and unique geometry. Thus, a computer acquires data describing an object and its surroundings, constructs a computer-based three dimensional model of the object from that data, superimposes an ideal geometry on the computer-based model, alters the ideal geometry to fit the form and function required of the reproduction, and then guides a milling machine in the fabrication of the reproduction. In contrast to the prior art, the present invention does not require human intervention in the reproduction process.

The present invention provides two preferred embodiments for the automated high precision reproduction of objects of complex and unique geometry. Both embodiments can machine reproductions solely from generic forms stored in the computer, thus eliminating the need for scanning. Alternatively, the reproductions may be machined solely from scanned data, without resort to generic forms stored in the computer.

FIRST PREFERRED EMBODIMENT

The first preferred embodiment discloses a method for scanning three dimensional objects and recording the resulting coordinates into a computer. The method comprises positioning a scanning head for recording X and Y coordinates nearest the center of the object being scanned. Once positioned, the Z coordinate is determined. The X, Y, and Z coordinates are recorded into the computer. The head is re-positioned, and additional X,Y,Z coordinates are recorded. This process repeats itself until a complete radial scan line is recorded into the computer. The object is rotated so another radial scan line can be recorded. The process repeats until the surface of the object is recorded into the computer as a set of coordinates. These coordinates may be filtered in the computer to eliminate noise by eliminating any coordinates corresponding to points not substantially proximate to the radial scan lines.

The first preferred embodiment discloses a method of generating parting lines in a computer such that a surface representation of a three dimensional object stored in a computer is divided into a plurality of regions. These regions prevent undercuts during a machining process. The method comprises finding an X,Y,Z coordinate on a radial scan line nearest the center of the object. A point is found on the radial scan line with a largest Y distance from the Z axis. Coordinates on the radial scan line below the parting point are clipped from the line.

The first preferred embodiment discloses a method for superimposing coordinates scanned from a three dimensional object onto a generic form stored in the computer of the object to create an altered generic set of coordinates. The generic form, which is comprised of a generic set of coordinates, is retrieved from database in the computer. The generic form is spatially rotated in the computer, such that it corresponds to a spatial orientation of the scanned coordinates. The generic form is scaled in the computer, such that the generic coordinates are sized substantially the same as the scanned coordinates.

The scaling step comprises scaling the generic coordinates in the computer as a function of measurements made of other objects in proximity to the scanned object. These measurements can include gap measurements between the scanned object and the proximal objects, height measurements for the scanned object or proximal objects, and width measurements for the scanned objects or the proximal objects.

Additional coordinate may be selectively created in the altered generic set of coordinates to emphasize features of either the generic form or the scanned object. The method of adding feature coordinates comprises first identifying feature coordinates within the coordinate set. The feature coordinates are plurally represented within the coordinate set by computing a plurality of parametric curves through the coordinate. This prevents the feature from being smoothed out or eliminated.

The coordinates may also be modified in the computer using a shaping function.

The coordinates may be further modified in the computer, when other objects exist in proximity of the scanned object, to ensure that any interference between the object and the proximal objects is avoided.

The first preferred embodiment discloses a method of generating a plurality of contour lines in a computer. The contour lines provide the tool paths for a machine tool. The radial scan lines are reparameterized in the computer to ensure that each radial scan line has substantially the same number of coordinates. The coordinates are connected between adjacent radial scan lines according to the order of the coordinates. These connections are the contour lines.

The contour lines may be selectively altered to provide a predetermined offset from the object surface for the tool paths. The contour lines may be selectively altered in regions selected by the computer or in regions selected by an operator. The selectively altering step comprises selecting an offset angle and an offset height from the contour line stored in the computer. An offset distance is determined from the offset angle and the offset height. A data point is projected from the contour line onto a plane to simplify normal vector calculation. A normal vector is calculated at the data point. A new offset data point is determined by shifting the data point the offset distance along the normal vector.

A tool path computation may be performed in the computer to prevent the machine tool from erroneously intersecting with the object surface. The computation comprises checking the minimum radii of principal curvature at a plurality of vertices of the tool paths. Those vertices where the minimum radius is smaller than a radius of the machine tool are identified. A curve of intersection with a plane is found for each the identified vertex. The plane passes through the identified vertex and contains one vector normal to the object surface area and another vector in the direction of the minimum radius. A plurality of line segments of an intersection curve are generated, which line segments intersect together. The line segments are subdivided by means of a segmentized searching circle until an error value between the line segments and the object surface area approaches a predetermined tolerance value. A segmentized searching circle is computed for both the current and an adjacent surface area. An intersection between triangular segments of each of the segmentized searching circles is found. The triangular segments are bisected and an intersection between them is determined. Additional segmentized searching circles are computed, and the intersection between them determined, until an error value between the intersected edges of the triangular segments and the object surface area approaches the pre-determined tolerance. The segmentized searching circles are propagated until they meet or until the boundaries of the object surface area are encountered. A new vertex is selected, a curve of intersection is found, and the process is repeated, until all of the identified vertices are processed.

SECOND PREFERRED EMBODIMENT

In a second preferred embodiment, an object is scanned and the resulting coordinates recorded into a computer. Two methods of scanning may be used.

In a first scanning method, a plurality of points are projected onto the object. The points are used to generate a set of coordinates, which are recorded into the computer. The points are converted to a plurality of profile lines in the computer. These coordinates may be filtered to eliminate noise by eliminating any of the coordinates corresponding to points not substantially proximate to the profile lines. The coordinates may be modified to ensure that each of the profile lines has substantially the same number of coordinates as an adjacent profile line.

In a second method of scanning, a plurality of profile lines are projected onto the object. The profile lines are scanned to generate a set of coordinates, which are recorded into the computer. The coordinates may be filtered in the computer to eliminate noise. The coordinates may be modified to ensure that each of the profile lines has substantially the same number of coordinates.

After the coordinates are recorded into the computer, they may be superimposed onto generic forms stored in the computer to create an altered generic set of coordinates. The generic form is retrieved from a database on the computer, which generic form is comprised of a generic set of coordinates. The generic form is spatially rotated in the computer, such that it corresponds to a spatial orientation of the object. The generic form is scaled, such that the generic set of coordinates is sized substantially the same as the object. Scaling comprises altering the generic coordinates as a function of measurements of other objects in proximity to the scanned object. These methods include measuring gaps between the scanned object and other proximal objects, measuring the height of other proximal objects, and measuring the width of other proximal objects. The generic form, i.e., the generic coordinates, are further modified using the scanned coordinates.

Additional coordinates may be selectively generated to emphasize features of either the object or the generic form. Additional coordinates are generated by identifying the coordinates of the feature and plurally representing the feature coordinates, for example, by computing a plurality of parametric curves through the feature coordinate. This prevents the feature from being smoothed out or eliminated by contouring or other modifying functions.

Coordinates may also be modified, when there are objects in the proximity of the scanned object, to ensure that any interference between objects is avoided.

When multiple sets of coordinates are used, they are connected at a common edge, when said common edge exists, to creating a master set of coordinates.

A plurality of surface patches are computed from the master set of coordinates. The method of computing comprises deriving a plurality of parametric curves from the master set of coordinates. Surface patches are computed from the parametric curves. The surface patches are combined into a three dimensional surface representation for machining.

Parting lines are generated in the computer such that the surface patches are divided into a plurality of regions. The creation of these regions prevent undercuts by the machine tool in the machining of the reproduction of the object.

The parting lines are generated by finding those surface patches through which the parting line passes, wherein an edge on the surface patch has end points with different signs of surface normal component values parallel to an axis of the machine tool. A seed point is found on the edge at which the component of the surface normal vector parallel to the machine tool axis is zero. The seed point on the edge may be found by bisecting the edge. The parting line is propagated by means of a segmentized searching circle until an edge of an adjacent surface patch is encountered. An edge point of the adjacent is identified and replaces the seed point. The parting line is propagated in the same manner until all the surface patches have been processed.

The method of propagating parting lines by a segmentized searching circle comprises generating a plurality of enclosing points about the seed point. A plurality of line segments are derived between the enclosing points, such that the seed point is enclosed by a substantially polygonal representation of the segmentized searching circle created by the line segments. A line segment which intersects the parting line is found. The intersecting line segment is subdivided into a plurality of smaller line segments. A new line segment is found and further subdivision occurs. This repeats until an end point of the line segment is located substantially proximate to the parting line. The end point replaces the seed point, and the steps are repeated until an edge of an adjacent the surface patch is encountered.

The surface patches within each region are contoured to create a plurality of contour lines. The contour lines provide the tool paths for the machine tool. The contouring method comprises identifying the surface patches through which a contour line passes. One edge of the identified surface patches is identified, through which the contour line passes. A seed point is found on the edge, possibly by bisecting the edge. The contour line is propagated by means of a segmentized searching circle until all of the identified surface patches have been processed in the computer. The propagating method comprises generating a plurality of enclosing points about the seed point. A plurality of line segments are derived between the enclosing points, such that the seed point is enclosed by a substantially polygonal representation of the segmentized searching circle created by the line segments. A line segments which intersects the contour line is identified. The intersecting line segment is subdivided into a plurality of smaller line segments, which replace the original line segments. A smaller line segment which intersects the contour line is identified. The intersecting line segment is again subdivided. This process repeats itself until an end point of a line segment is located substantially proximate to the contour line. The end point replaces the seed point and the segmentized searching circle method repeats until an edge of an adjacent surface patch is encountered.

The contour lines may be selectively altered to provide a predetermined offset from the surface patches for the tool paths. The contour lines may be selectively altered in regions selected by the computer or in regions selected by an operator. The selectively altering step comprises selecting an offset angle and an offset height from the contour line stored in the computer. An offset distance is determined from the offset angle and the offset height. A data point is projected from the contour line onto a plane to simplify normal vector calculation. A normal vector is calculated at the data point. A new offset data point is determined by shifting the data point the offset distance along the normal vector.

A tool path computation may be performed in the computer to prevent the machine tool from erroneously intersecting with the surface patches. The computation comprises checking the minimum radii of principal curvature at a plurality of vertices of the surface patches. Those vertices where the minimum radius is smaller than a radius of the machine tool are identified. A curve of intersection with a plane is found for each the identified vertex. The plane passes through the identified vertex and contains one vector normal to the surface patch and another vector in the direction of the minimum radius. A plurality of line segments of an intersection curve are generated, which line segments intersect together. The line segments are subdivided by means of a segmentized searching circle until an error value between the line segments and the surface patch approaches a pre-determined tolerance value. A segmentized searching circle is computed for both the current and an adjacent surface patch. An intersection between triangular segments of each of the segmentized searching circles is found. The triangular segments are bisected and an intersection between them is determined. Additional segmentized searching circles are computed, and the intersection between them determined, until an error value between the intersected edges of the triangular segments and the surface patches approaches the predetermined tolerance. The segmentized searching circles are propagated until they meet or until the boundaries of the surface patches are encountered. A new vertex is selected, a curve of intersection is found, and the process is repeated, until all of the identified vertices are processed.

BOTH EMBODIMENTS

Machine tool commands are generated, directing the machining of a workpiece material into the reproduction within a predetermined tolerance. These commands, for example, can optimize the step length along the tool paths, the scallop height, and other parameters.

The step length optimization comprises checking an error value between the tool path and the surface patch, and dividing the step length until the error value is smaller than a pre-determined tolerance. The tool path can also be optimized by determining a cutter size for the machine tool in the computer based on the characteristics of the machine tool, a feed rate, a depth of cut, a spindle speed, and the characteristics of the material.

The machine tool performance can be optimized by calculating the scallop height for the material based on a plurality of machining parameters. The parameters used consist of the characteristics of the tool path, the distance between adjacent tool paths, the spindle speed, the feed rate, the characteristics of the material, and the cutter size. The scallop height is compared to a predetermined boundary value, and the machining parameters may be altered when the scallop height exceeds the boundary value.

The material to be shaped into the reproduction must be fixtured so that it may be machined sequentially by regions, usually through the alternate orientation of the material. The fixturing method comprises selecting a workpiece blank or appropriate size. The blank may be selected from a plurality of pre-formed blanks, such that the need for multiple machining of each region is eliminated, thereby speeding the machining process. These pre-formed blanks may be selected automatically by the computer. The blank is oriented on the fixture according to a spatial orientation of the region in the computer. The fixture secures the blank on a bed surface to prevent movement of the blank during machining. The blank is re-orient and re-machined for each region, as needed.

Once the blank is selected and oriented, the tool paths and commands are transmitted from the computer to the machine tool. The machine tool is directed to machine the material by the region into the reproduction of the object. The tool paths for each region are transmitted separately and the blank machined accordingly.

DESCRIPTION OF THE DRAWINGS

In the drawings, where like numerals refer to like elements throughout the several views.

FIG. 2 is a system description flow chart for the first preferred embodiment;

FIG. 3 is a flow chart describing a data acquisition method for the first preferred embodiment;

FIG. 6 illustrates a plurality of unwrapped radial scan lines;

FIG. 12 describes a dental prosthesis fitted over a prepared tooth;

FIG. 22 illustrates a generic form as a series of profile lines;

FIG. 39 illustrates the optimization of tool path scallop heights in both preferred embodiments;

FIGS. 42A, 42B, 42C, and 43 illustrate machining, rough cutting, and finish cutting in both preferred embodiments.

DETAILED DESCRIPTION OF THE PREFERRED EMBODIMENTS

In the following detailed description of the invention, reference is made to the accompanying drawings which form a part hereof, and in which is shown by way of illustration two preferred embodiments in which the invention may be practiced. It is to be understood that other embodiments may be utilized and structural changes may be made without departing from the scope of the present invention.

At the end of the following detailed description of the invention, an appendix of citations can be found. This appendix discusses in detail the technical background information and specific mathematics involved in both preferred embodiments of the present invention. The citations in the appendix are hereby incorporated by reference for the purpose of providing demonstrative evidence of the level of skill in the art.

HARDWARE COMPONENTS

Figure 1:
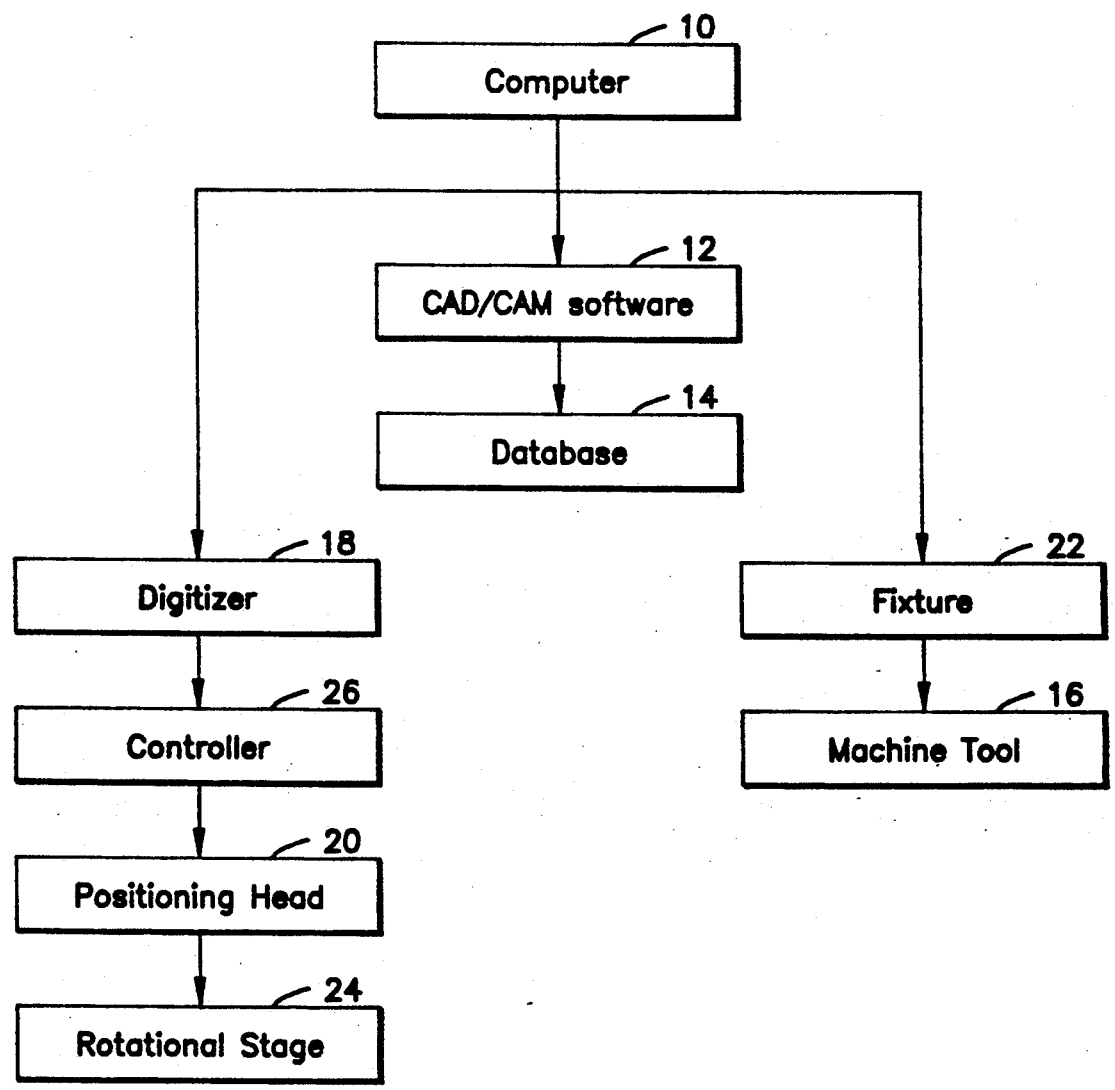
FIG. 1 illustrates the hardware components of the present invention.

FIG. 1 describes the components of the present invention. These components include a computer system 10, Computer-Aided-Design/Computer-Aided-Manufacturing (CAD/CAM) software 12, a database of generic forms 14, a machine tool 16, and a digitizer 18. The computer 10 is a UNIX-based work station built by Silicon Graphics, Incorporated. The CAD/CAM software 12 is a custom package that creates a computer-based model of the object, manipulates the model, and generates commands directing the machine tool 16 to reproduce the object. The database 14 is comprised of files storing generic object forms that provide a plurality of idealized versions of the object. The machine tool 16 is a three axis milling machine built by Servo Products Company. The digitizer 18 is an optical, non-contact, three dimensional, surface digitizer 18 built by Laser Design Corporation. Using these components, the present invention can machine reproductions of objects of complex and precise geometry.

THE FIRST PREFERRED EMBODIMENT OF THE CAD/CAM SOFTWARE

FIG. 2 describes the method steps used in a first preferred embodiment of the CAD/CAM software 12. The object is radially scanned and the resulting coordinates are recorded into the computer (28). Radial scan lines appear to start near the center of the top of the object and proceed outward toward the bottom of the tooth. Initially, the coordinates are stored in an "unwrapped" state as successive scan lines. The radial scan lines are "clipped" to determine a parting line (30). The radial scan lines are then "wrapped" about the Z-axis to obtain a three dimensional representation of the object (32). The scanned coordinates may be superimposed onto a generic form of the object stored in the computer, thus creating an altered generic set of coordinates (34). Contour lines are created by connecting corresponding points on adjacent radial scan lines (36). The contour lines may be projected in a normal direction to the surface to create the offset tool paths for the machine tool (38). Multiple offset tool paths may be generated to provide rough and finish cutting planes, and to achieve a desired machining tolerance. Tool interference checks are made to eliminate gouging (40). Additional machine tool commands are generated in the computer as required (42). The material to be machined is fixtured such that it may be machined sequentially by region (44). The offset tool paths and commands are then transmitted from the computer to the machine tool for the machining step (46).

DATA ACQUISITION

FIG. 3 describes a method of data acquisition in the first preferred embodiment. Data acquisition is the first step in generating a computer-based representation of a three dimensional object. In the first preferred embodiment, the digitizer 18 is a point-by-point triangulation system. As described in FIG. 1, the digitizer 18 is comprised of a three axis positioning head 20 with a low energy laser source and detector, a rotational stage 24, and a computer controller 26. The controller 26 positions both the rotational stage 24 and the positioning head 20 (48). An object is placed on the rotational stage 24, and the laser beam reflects from it. The reflected laser beam is used to measure the distance between the object and the laser source (50). The (Z) coordinate on the surface is established by combining the position of the laser source with the determined distance between the object and the laser source. The computer 10 records the head 20 position into the database 14 as (X,Y,Z) coordinates (52). These coordinates are stored in an "unwrapped" state. The digitizer 18 creates radial scan lines by beginning near the center of the top of the object and moving radially outward from the object. The controller 26 orders either the rotational stage 24 or the positioning head 20 to shift to a new (X,Y) position to obtain a new (Z) value (54). The controller 26 orders the rotational stage 24 to rotate to start a new line (56). In this manner, the surface of the object is scanned and represented by a grid of (X,Y,Z) position coordinates (58). For objects with undercuts or similar features such as vertical walls, the rotational stage 24, or just the object itself, may be set at any angle relative to the laser source for scanning. If such an object is not angled during the scan, data may be lost. For example, the digitizer 18 may erroneously sense that an edge of the object has been reached and stop scanning. Data can be obtained at variable step sizes, with a minimum step size of 8 microns. The surface can be scanned at approximately ten to thirty points per second. Maximum digitizing volume is six inches by six inches by three inches. The CAD/CAM software 12 may filter the coordinates to eliminate noise (60). Filtering eliminates any coordinates that correspond to points not substantially proximate to the radial scan line (60).

The data acquisition method used in the first preferred embodiment is well suited to the fabrication of dental prostheses. Each patient presents a unique set of teeth shapes and sizes. Thus, each restoration has a unique form, depending upon the history of decay, fracture, and previous restorations. The data required to produce the dental prosthesis includes: (1) the configuration of the tooth prepared by the dentist to receive the prosthesis; (2) the gap between, the heights of, and the widths of, the adjacent teeth which provides the scaling factor; (3) the surface configuration of the opposing teeth with which the prosthesis must occlude; and (4) motion of the mandible relative to the maxilla during function (in the areas where any of the teeth remain in contact and therefore guide the motion of the jaws). With the first preferred embodiment, the process to create a dental prosthesis begins in a similar fashion as the traditional wax casting techniques discussed hereinbefore. A dentist makes an impression of the two arches of teeth. The impression is a three-dimensional negative of the teeth shapes. The dentist creates a model duplicating the teeth by pouring plaster into the impression. When the plaster has set, the impression is discarded. The digitizer 18 scans the plaster model and records the resulting coordinates into the database 14.

PARTING LINE GENERATION

Figure 4:
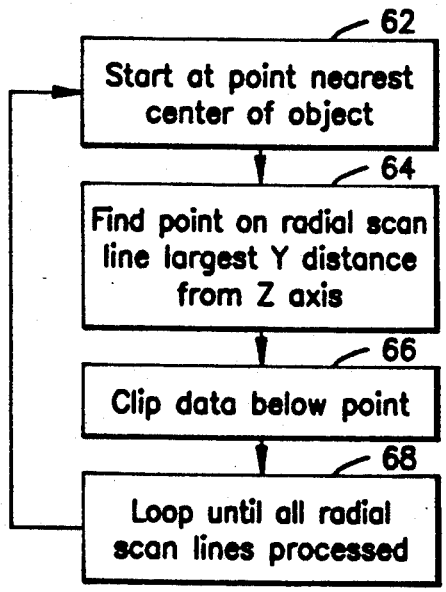
FIG. 4 is a flow chart describing a parting line for the first preferred embodiment.

FIG. 4 describes a method for generating parting lines in the first preferred embodiment. After recording the coordinates for the radial scan lines, a parting line is generated so that undercuts and their associated interferences are avoided during the machining step. Initially, the coordinates are stored in an "unwrapped" state as successive scan lines. Starting at a point nearest the center of the object (62), a search is made for a point on the radial scan line with the largest Y-axis distance from the Z-axis (64). The first point with the largest Y-axis distance (i.e., the relative maximum) is a point on the parting line. A parting line is generated by "clipping" data on each of the radial scan lines below the selected parting line (66). Each of the successive radial scan lines are processed in a similar manner to form the complete parting line (68).

Figure 5A:
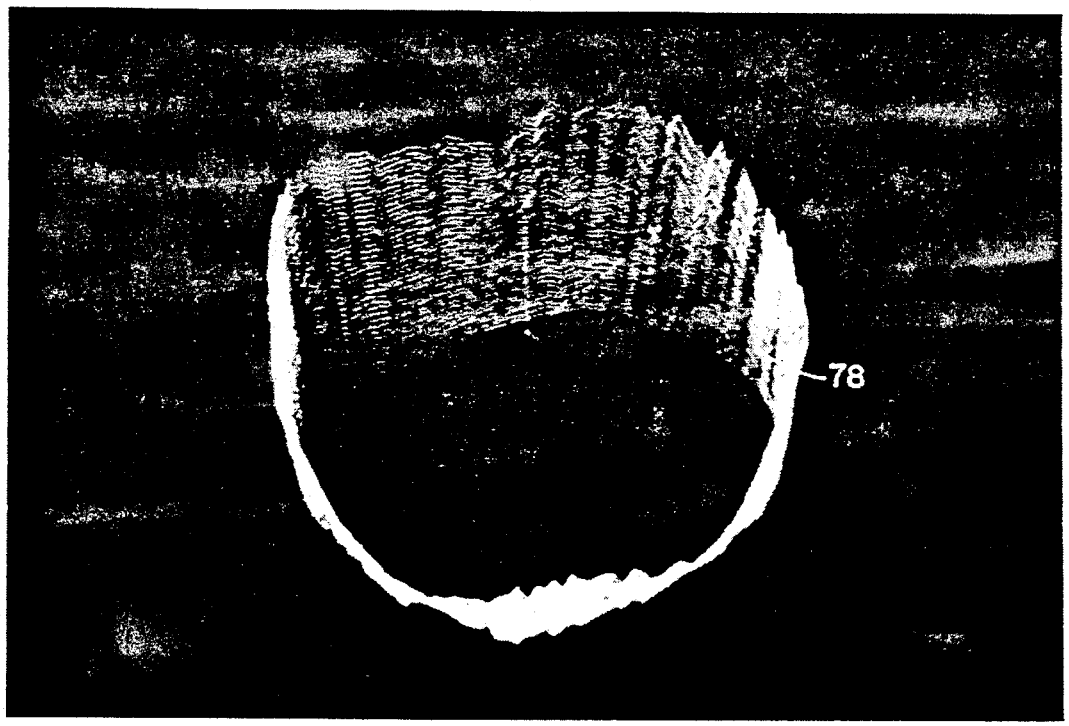
FIG. 5A illustrates the ruled surface connecting the generic form and prepared tooth surface.
Figure 5B:
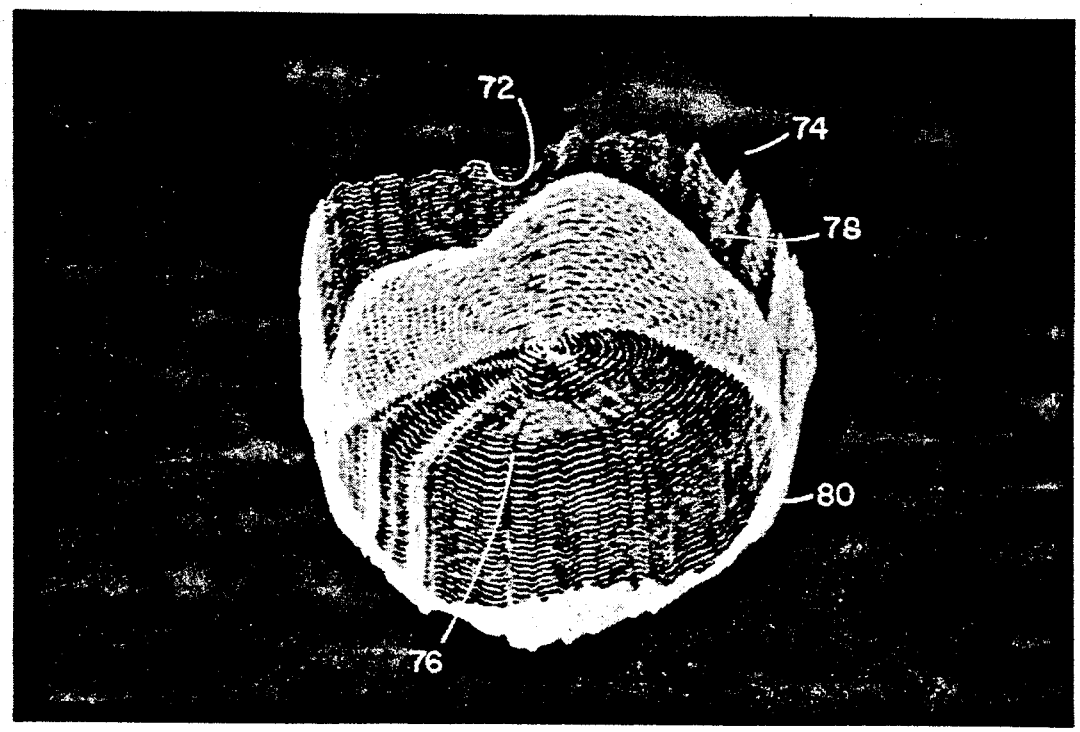
FIG. 5B illustrates the computer-based representation comprised of an altered generic form, a prepared tooth surface, and a ruled surface connecting the generic form and prepared tooth surface.

As illustrated in FIGS. 5A and 5B, a single parting line 72 in the first preferred embodiment typically defines two major regions for a dental prosthesis 70. Both FIGS. 5A and 5B are contour line representations, discussed herein later, of the dental prosthesis 70. One region is a generic form 74 representing the occlusal surface and sides of the prosthesis 70 to the crests of convexity (the two maximum horizontal points in any given radial scan line to the parting line). The generic form 74 is altered to fit the space available in the patient's mouth. The other region is a prepared tooth surface 76 representing the lower part of the configuration. The prepared tooth surface 76 of the prosthesis 70 is manipulated to fit over the prepared tooth. Also included in this region is a connecting surface 78 between the generic form 74 and the prepared tooth surface 76, i.e., the surface below the crest of convexity, typically extending from the parting line 72 of the generic form 74 to the margin 80 of the prosthesis.

DATABASE OF GENERIC FORMS

Figure 7A:
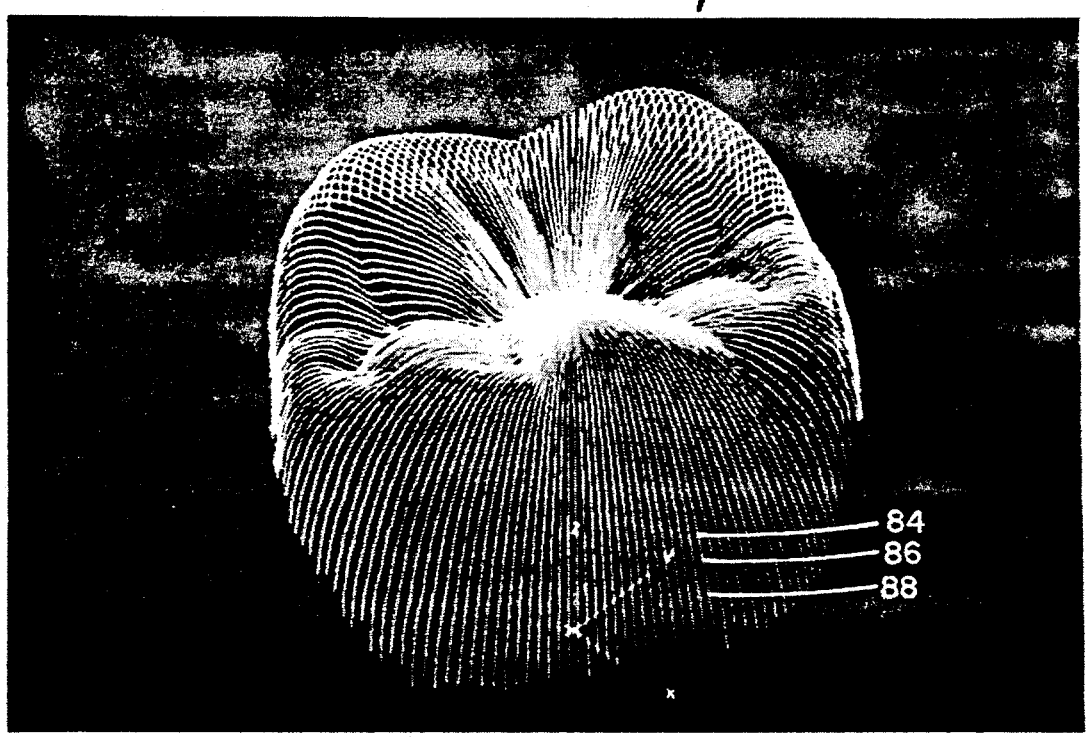
FIG. 7A illustrates a plurality of wrapped radial scan lines comprising the generic form.
Figure 7B:
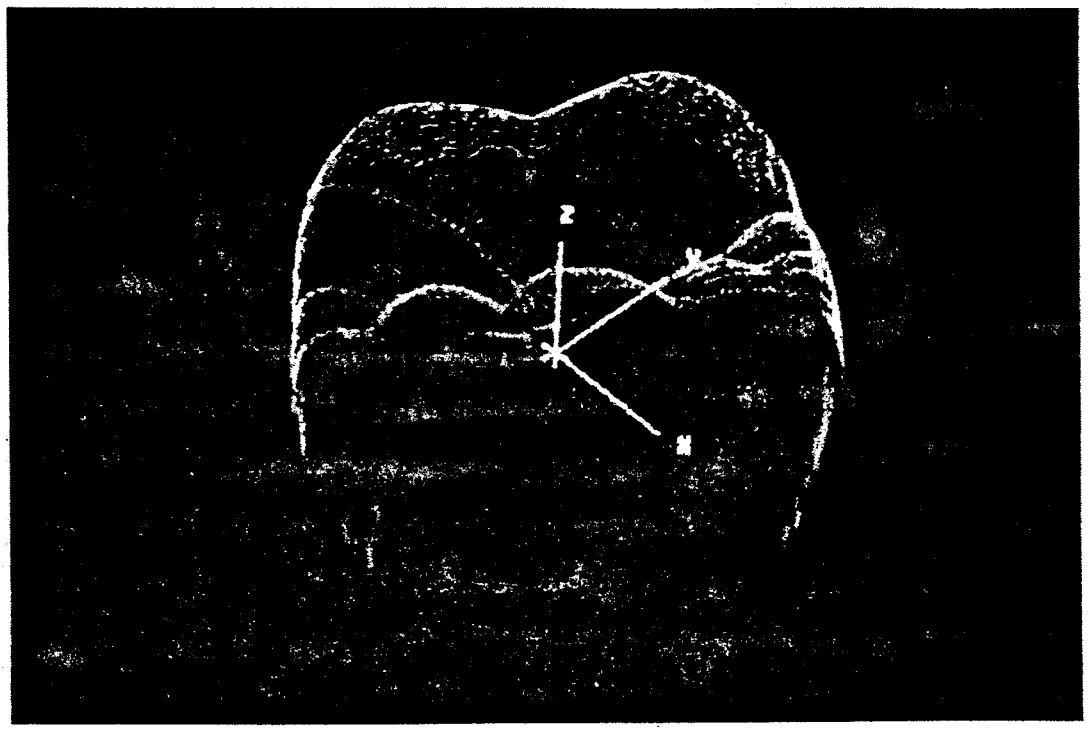
FIG. 7B illustrates a plurality of contour lines generated for the generic form.

When data acquisition and parting line generation are complete, the first preferred embodiment of the CAD/CAM software generates a set of data files so a computer-based model of the three dimensional object can be stored on the computer. FIG. 6 is an illustration of the radial scan lines stored in an "unwrapped" state. FIG. 7A is an illustration of the "wrapped" radial scan lines.

The surface 82 of the object is represented as a plurality of points 86 and 88 on a plurality of radial scan lines 84. Each radial scan line 84 appears to start near the center of the top of the object and proceed outward. Each of the radial scan lines 84 are at different angular increments around the center of the object. Thus, each radial scan line 84 functions as a planar slice or cross-section of the three dimensional surface 82 beginning at the center of the object and extending to the outer surface.

Usually, the database contains a plurality of standardized object representations, referred to as generic forms. A generic form is comprised of a generic set of (X,Y,Z) coordinates. The generic form permits the fabrication of reproductions based on idealized or standardized geometries. Like the scanned objects, the surface of each generic form 82 is represented in the computer 10 as a plurality of points 86 and 88 on a plurality of radial scan lines 84. Each radial scan line 84 appears to start near the center of the top of the generic form 82 and proceed outward. Each of the radial scan lines 84 are at different angular increments around the center of the generic form 82. Thus, each radial scan line 84 functions as a planar slice or cross-section of the three dimensional surface beginning near the center of the generic form 82 and extending to the outer surface.

When the first preferred embodiment is used to produce dental prostheses, the database contains a plurality of standardized generic tooth forms. The generic tooth forms used are typically computer-based representations of standardized plaster models of teeth.

SUPERPOSITION OF GENERIC FORM

Figure 8:
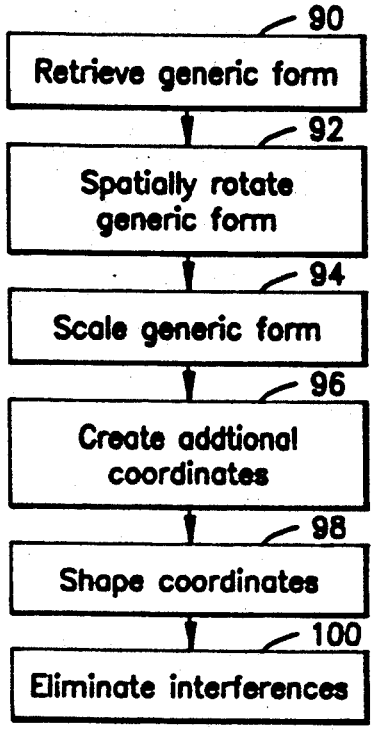
FIG. 8 is a flow chart describing a superposition method in the first preferred embodiment

FIG. 8 describes a method for superimposing the scanned coordinates onto a generic form stored in the database. Landmarks on the generic form are matched with, and compared to, corresponding landmarks on the scanned object, thereby providing a correct orientation and size for the generic form. The CAD/CAM software retrieves a generic form from the database (90). The generic form is "spatially rotated" and positioned so that it corresponds to a spatial orientation of the set of coordinates scanned from the object (92). This orientation is performed by matching at least three landmarks on the generic form with corresponding landmarks on the scanned object. The CAD/CAM software also scales the generic coordinates so they are sized substantially the same as the scanned coordinates (96). Additional coordinates may be created to prevent features from being smoothed out or eliminated (96). The resulting representation may be shaped if desired (98). The representation may also be checked for interferences with other objects adjacent to where the reproduction will reside (100).

Figure 9:
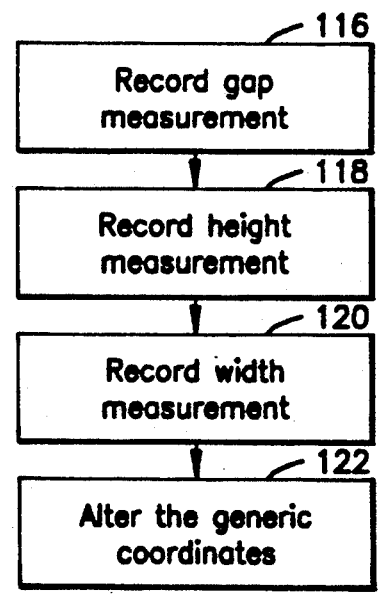
FIG. 9 is a flow chart describing a scaling method in the first preferred embodiment.

FIG. 9 describes the scaling operation performed on the generic form. Gap measurements are recorded between the object and other objects adjacent to it (116). Also recorded are height and width measurements of the object and/or adjacent objects (118 and 120). The ratio of these values to the equivalent distances on the generic form yields a scaling factor. This scaling factor may be applied to the set of coordinates to create a linear transformation of the coordinates (122). Thus, the generic form can be sized to fit the space available for the reproduction. Note that with this method, a replacement part may be created using the computer-based generic form scaled according to the "gap" left for its placement, and from measurements of adjacent objects. Thus, the original object is not required when machining replacement parts, unless it is desired to construct a true, substantially identical "reproduction" of the object.

Figure 10:
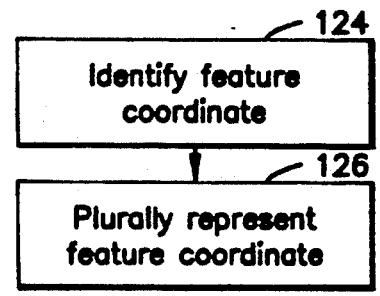
FIG. 10 is a flow chart describing a method for emphasizing features in the first preferred embodiment.

FIG. 10 describes a method for creating additional feature coordinates in the first preferred embodiment. Additional coordinates can be added to the set of coordinates to emphasize features of the object or the generic form. The additional coordinates ensure that the feature is not smoothed out, or otherwise eliminated, either by system operators or by the CAD/CAM software. A feature coordinate is identified within the set of coordinates (124). The CAD/CAM software plurally represents the feature coordinate by computing a plurality of parametric curves extending through the feature coordinate (126). These parametric curves are used to provide additional coordinates, thereby preventing the feature from being smoothed out or eliminated.

Figure 11:
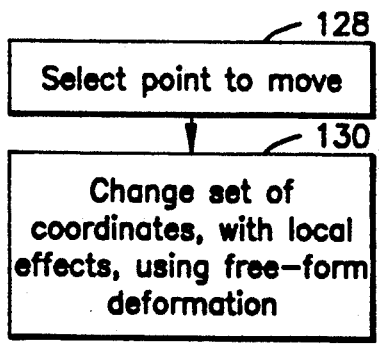
FIG. 11 is a flow chart describing a method for shaping generic forms in the first preferred embodiment.

FIG. 11 describes a method for shaping the generic form in the first preferred embodiment. Using this method, a point on the surface represented by a coordinate is selected and moved to a new position (128). The set of coordinates can be changed, with local effects, using a free-form deformation technique (130). The surface geometry is deformed using a shaping function. The deformations decrease radially about the point of interest. Points very near the moved point will move almost as much. Points further away will move less, as determined by the selected shaping function, decreasing to zero movement at the selected maximum radius. This provides the equivalent of a computer shaping tool for the system operator.

When the first preferred embodiment is used to produce dental prostheses, it incorporates information from both the scanned tooth and from the generic tooth form. FIG. 12 illustrates this incorporation. A generic tooth form 136 stored in the database contains a local coordinate system 140, based on maximum height (in the occlusal plane) of the cusp tips. The database also contains the positions of the proximal contacts 142 and 144 relative to that local coordinate system 140. If a landmark 146 is placed on the prepared tooth 148, a local coordinate system 150 relative to the prepared tooth 148 can be calculated. Since the two contact points 142 and 144 on the prosthesis must match the two contact points on the proximal teeth, a transformation from the generic coordinates to the prosthesis coordinates can be made. With this transformation, a scaled generic form 136 is created for the prepared tooth configuration 148.

Figure 13B:
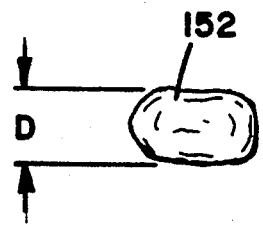
FIGS. 13A and 13B illustrate the dimensions that decide the scaling factor.
Figure 13A:
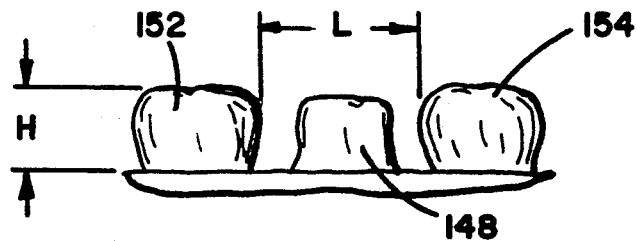

The design of the surfaces of the prosthesis is more complicated than simply transforming the coordinate system. The occlusal surface of the prosthesis is suggested by the generic tooth form stored in the database 14. However, as illustrated by FIGS. 13A and 13B, the prosthesis must contact the adjacent teeth 152 and 154. To accomplish this, the CAD/CAM software scales the generic tooth form so that the mesial-distal distance between proximal teeth matches the distance between contact points of the generic form. The scaling factor used is simply the ratio of actual mesial-distal length over the mesial-distal length of the generic form. Thus, the size of the generic form can be altered by checking the gap between the adjacent teeth 152 and 154. The width and height of the generic form can be determined by measuring the thickness and height of the adjacent teeth 152 and 154. Also, the coordinates representing the fossae and cusps of the occlusal surface may be altered to raise or lower the cusps. This scaling factor is most likely provided by measuring the upper and lower teeth while in occlusion.

Figure 14A:
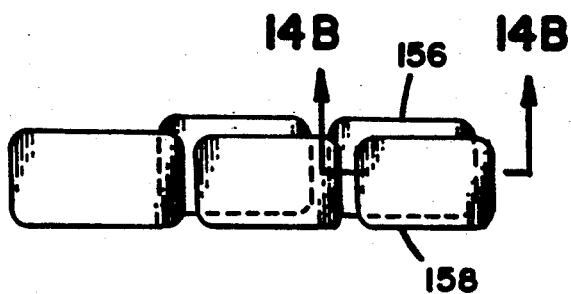
FIGS. 14A and 14B illustrate an interference check between adjacent objects.
Figure 14B:
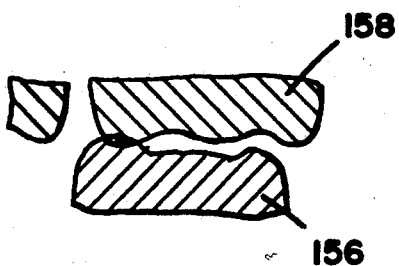
Figure 15:
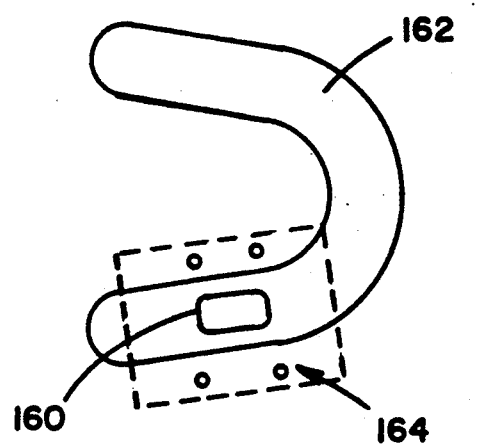
FIG. 15 illustrates a digitized impression.

FIGS. 14A and 14B show that the interference between the upper and lower teeth can be checked by using contour lines. Interferences are solved by moving the coordinates involved. The occlusal surface of the prosthesis 156 is checked when the maxilla tooth 158 is in contact. First, the relative positions between mandible and maxilla teeth have to be found. FIG. 15 illustrates the data collection method. Impressions 160 in a wax plate 162 are digitized to find the relative position between the mandible and maxilla teeth. Landmarks 164 are plugged into the impression 160. The mandible and maxilla teeth can be digitized from opposite sides of the impression 160. Also, the position of the landmarks 164 are digitized. Thus, the relative position of the mandible and maxilla teeth can be calculated based on the position of the landmarks 164.

As described by FIG. 12, the lower part of the prosthesis 134 fits over the prepared tooth 148. This prepared tooth surface 134 must be connected to the generic form providing the occlusal surface 136. Typically, a ruled surface 138 (e.g., straight, ruled lines) is generated from the margin of the prepared tooth surface to the parting line of the prosthesis. The resulting margin of the prosthesis is usually sharp. A small error near the edge could cause severe problems, such as too loose or too tight a fit.

CONTOURING

Figure 16:
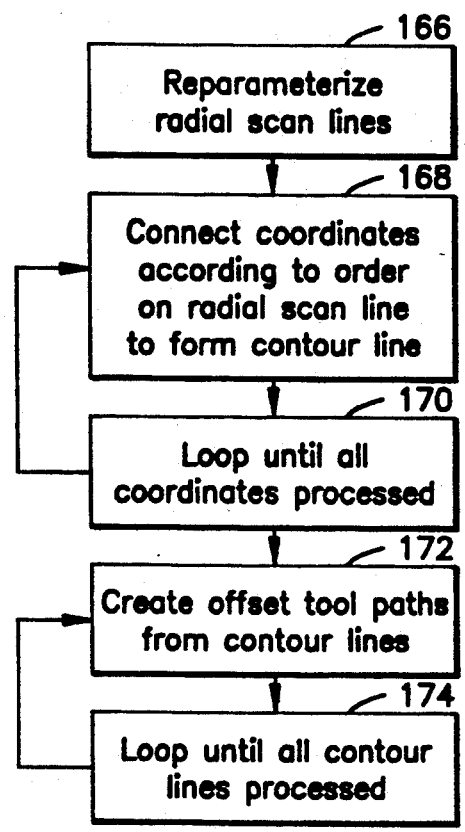
FIG. 16 is a flow chart describing a method for contouring in the first preferred embodiment.

FIG. 16 describes a method for contouring the generic object in the first preferred embodiment. Each radial scan line is reparameterized, so that all radial scan lines have the same number of coordinates (166). Contour lines are generated through these coordinates, matching the order of coordinates in each radial scan line (168). For example, the first coordinate point in the first radial scan line is connected to the first coordinate point in the second radial scan line, the second coordinate point in the first radial scan line is connected to the second coordinate point in the second radial scan line, etc. Thus, the contour lines are essentially perpendicular to the radial scan lines. These contour lines define the machine tool 16 contact point on the surface of the prosthesis. Enough contour lines are generated to connect all coordinates (170). The contour lines may be selectively altered to provide offset tool paths from the reproduction surface (172 and 174). Offset tool paths are generated in such a way as to prevent the machine tool 16 from erroneously intersecting with the surface of the prosthesis. Offsets can be applied to regions automatically selected by the CAD/CAM software. Alternatively, offsets can be applied to regions manually selected by a systems operator.

Figure 17:
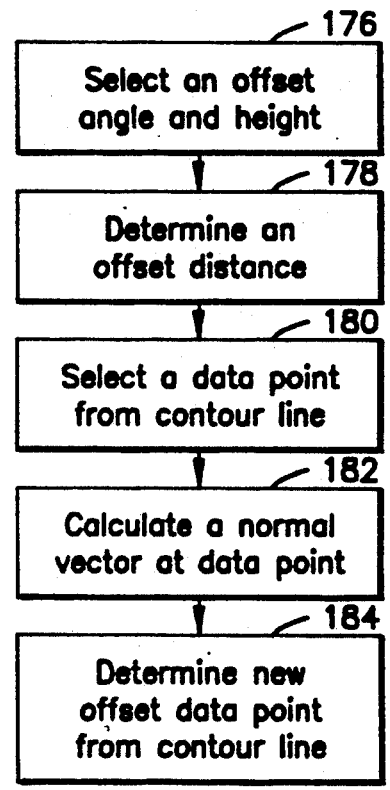
FIG. 17 is a flow chart describing a method for generating offset tool paths in the first preferred embodiment.

FIG. 17 describes a method for generating offset tool paths in the first preferred embodiment. The CAD/CAM software selects an offset angle and an offset height from the contour line (176). The offset angle and offset height can be selected arbitrarily. The offset angle and the offset height determine the offset distance (178). A data point is projected the offset distance from the contour line (180). The CAD/C software calculates the normal vectors to the contour lines at each coordinate point (182). The CAD/CAM software determines a new offset data point by shifting the data point offset distance along the normal vector from the contour line (184).

TOOL INTERFERENCE CHECK

Figure 18:
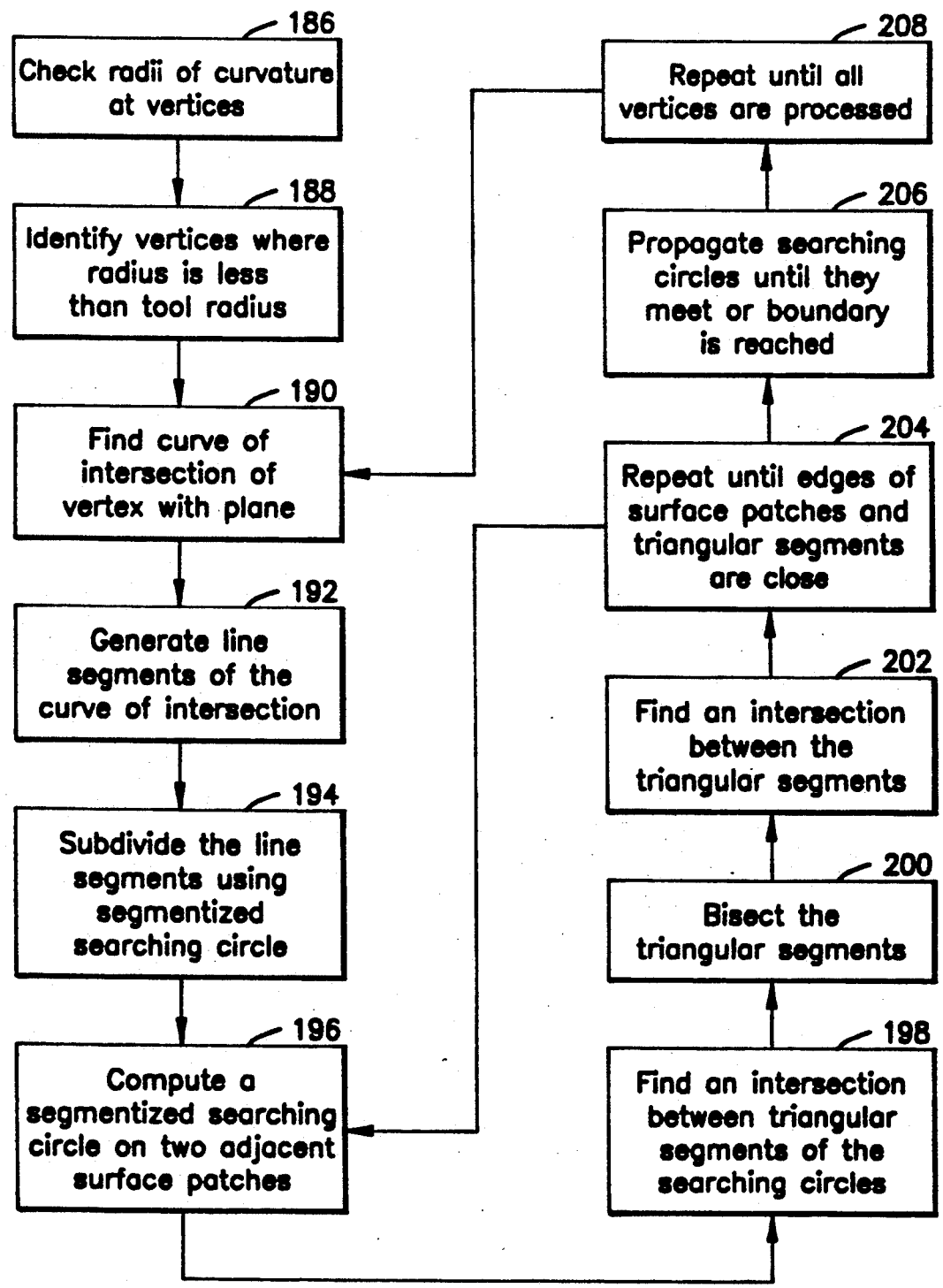
FIG. 18 is a flow chart describing a method of eliminating tool interferences in the first preferred embodiment.

FIG. 18 describes a method for preventing tool interferences in the first preferred embodiment. The CAD/CAM software performs a computation to prevent the offset tool paths from erroneously intersecting with the prosthesis surface represented by the original scan lines or the original contour lines. The CAD/CAM software checks the minimum radii of principal curvature at the vertices or coordinate points of the offset tool paths (186). The vertices where the minimum radius is smaller than the machine tool 16 radius are identified (188). The CAD/CAM software finds a curve of intersection of each identified vertex with a plane. The plane passes through the identified vertex and contains a first vector normal to the surface and a second vector in the direction of the minimum radius (190). A plurality of line segments of the intersection curve are generated, which line segments intersect together (192). The line segments are subdivided using a segmentized searching circle, described hereinbelow, until an error value between the line segments and the surface approaches a predetermined tolerance value (194). A segmentized searching circle is computed for the two adjacent surface areas (196). An intersection between a plurality of triangular segments of the segmentized searching circles is found (198). The triangular segments are bisected (200). An intersection between the triangular segments is formed (202). These steps are repeated (i.e., the segmentized searching circle computing step (196) through the intersection finding step (202)) until an error value between a plurality of intersected edges of the triangular segments and the surface approaches the predetermined tolerance (204). The segmentized searching circles are propagated until the circles meet or until the circles reach one of a plurality of boundaries for the surface areas (206). These steps are repeated (i.e., the curve of intersection finding step (190) through the segmentized searching circle propagating step (206)) until all identified vertices are processed (208).

THE SECOND PREFERRED EMBODIMENT OF THE CAD/CAM SOFTWARE

Figure 19:
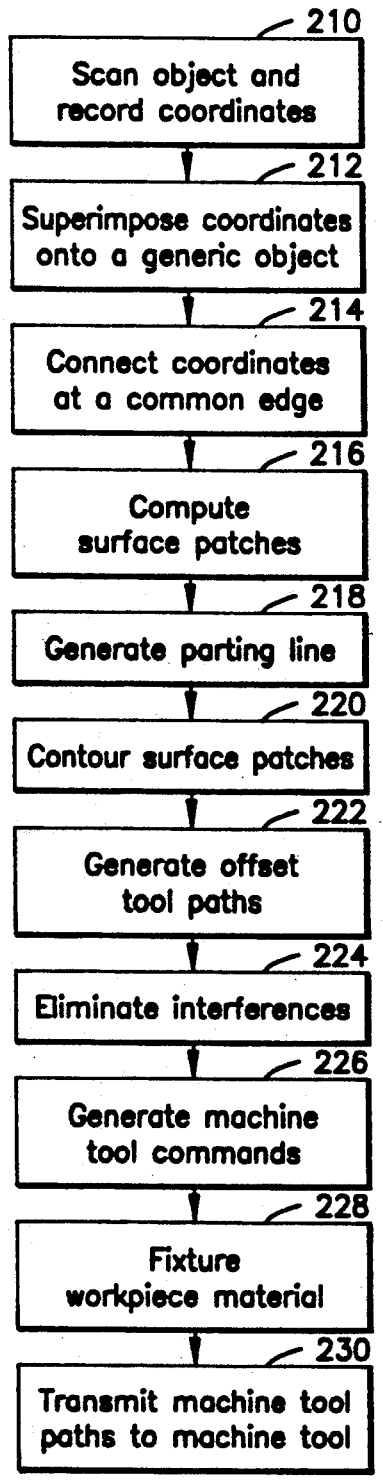
FIG. 19 is a system description flow chart for the second preferred embodiment.

FIG. 19 describes the method steps used in a second preferred embodiment of the CAD/CAM software. The object is scanned and coordinates describing the object are recorded into the computer (210). More than one set of coordinates may be recorded for each object. The set of coordinates may be superimposed onto a generic form of the object stored on the computer (212). The generic form is comprised of a generic set of coordinates. The superposition of the recorded coordinates thus creates an altered generic set of coordinates. If the object is represented by more than one set of coordinates, the sets are connected to create a master set of coordinates (214). A plurality of surface patches are computed from the master set of coordinates (216). Parting lines may be generated to divide the surface patches into a plurality of regions, thus preventing undercuts by the machine tool 16 (218). Contour lines are generated from the surface patches (220). Offset tool paths are generated from the contour lines that provide a predetermined offset from the surface patches for the machine tool 16 (222). A computation is performed on the offset tool paths to prevent the machine tool 16 from erroneously intersecting with the surface patches (224). Additional machine tool commands are generated in the computer 10 (226). The workpiece material is fixtured such that it may be machined sequentially by region (228). The offset tool paths and commands are transmitted from the computer 10 to the machine tool 16 (230).

DATA ACQUISITION

Figure 20:
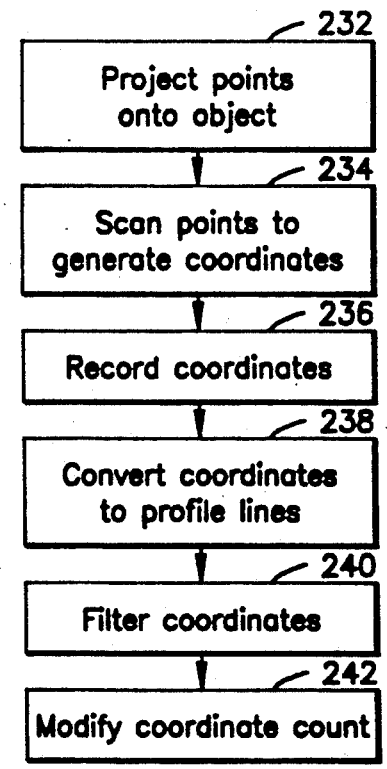
FIG. 20 is a flow chart describing a first data acquisition method for the second preferred embodiment.
Figure 21:
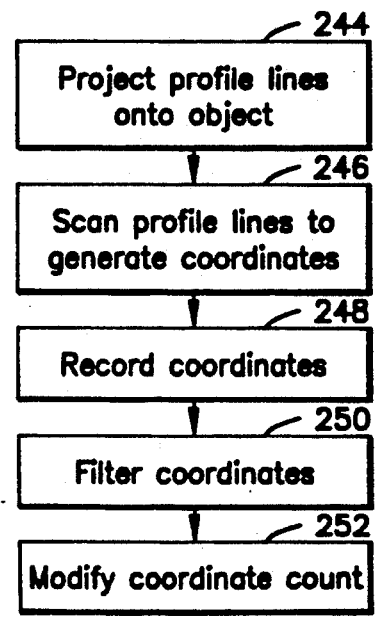
FIG. 21 is a flow chart describing a second data acquisition method for the second preferred embodiment.

FIGS. 20 and 21 describe two alternative methods of data acquisition in the second preferred embodiment. The digitizer is the same used in the first preferred embodiment. However, profile lines rather than radial scan lines are recorded for each object. Profile lines appear to be planar slices of the three dimensional surface of the scanned object.

In FIG. 20, the digitizer projects a plurality of points onto the object (232). The second preferred embodiment scans the three dimensional object (234) and records the resulting set of coordinates of points into the computer (236). More than one set of scanned coordinates can be created to represent each object. The CAD/CAM software converts the set of coordinates into a plurality of profile lines (238) and filters the set of coordinates to eliminate noise (240). Filtering eliminates any coordinates that correspond to points not substantially proximate to the profile lines. The scanned coordinates representing the profile lines are modified to ensure that each of the profile lines has substantially the same number of coordinates as adjacent profile lines (242).

In FIG. 21, the digitizer projects a plurality of profile lines onto the object (244). The three dimensional object is scanned (246) and the resulting set of coordinates is recorded into the computer (248). More than one set of coordinates can be created to represent each object. The CAD/CAM software filters the set of coordinates to eliminate noise (250). Filtering eliminates any coordinates that correspond to points not substantially proximate to the profile lines. The scanned coordinates representing the profile lines are modified to ensure that each of the profile lines has substantially the same number of coordinates as adjacent profile lines (252). The data acquisition method used in the second preferred embodiment, like that of the first preferred embodiment, is well suited to the fabrication of dental prostheses. Each patient presents a unique set of teeth shapes and sizes. Thus, each restoration has a unique form, depending upon the history of decay, fracture, and previous restorations. The data required to produce the dental prosthesis includes: (1) the configuration of the tooth prepared by the dentist to receive the prosthesis; (2) the gap between, the heights of, and the widths of, the adjacent teeth which provides the scaling factor; (3) the surface configuration of the opposing teeth with which the prosthesis must occlude; and (4) motion of the mandible relative to the maxilla during function (in the areas where any of the teeth remain in contact and therefore guide the motion of the jaws). In the second preferred embodiment, the process to create a dental prosthesis begins in a similar fashion as the traditional wax casting techniques discussed hereinbefore. A dentist makes an impression of the two arches of teeth. The impression is a three-dimensional negative of the teeth shapes. The dentist creates a model duplicating the teeth by pouring plaster into the impression. When the plaster has set, the impression is discarded. The digitizer scans the plaster model and records the resulting coordinates into the database.

DATABASE OF GENERIC FORMS

When data acquisition is complete, the second preferred embodiment of the CAD/CAM software generates a set of data files so a computer-based model of the three dimensional object can be stored on the computer. Figure 22 is an illustration of the profile lines.

The profile lines represent the surface of the object as a plurality of point 54 on a plurality of profile lines 256. Each of the profile lines 256 are at different increments along the surface of the object. Thus, each profile line 256 functions as a planar slice of the three dimensional surface of the scanned object.

In the second preferred embodiment, as in the first preferred embodiment, the database contains a plurality of standardized object representations, referred to as generic forms. The generic form is comprised of a generic set of (X,Y,Z) coordinates. The generic form permits the fabrication of reproductions based on idealized or standardized geometries. In the second preferred embodiment, the surface of each generic form is represented in the computer as a plurality of points 254 on a plurality of profile lines 256. Each of the profile lines 256 are at different increments along the surface of the generic form. Thus, each profile line 256 functions as a planar slice of the three dimensional surface of the generic form.

When the second preferred embodiment is used to produce dental prostheses, the database contains a plurality of standardized generic tooth forms. The generic tooth forms used are typically computer-based representations of standardized plaster models of teeth.

SUPERPOSITION OF IDEAL GENERIC FORM

Figure 23:
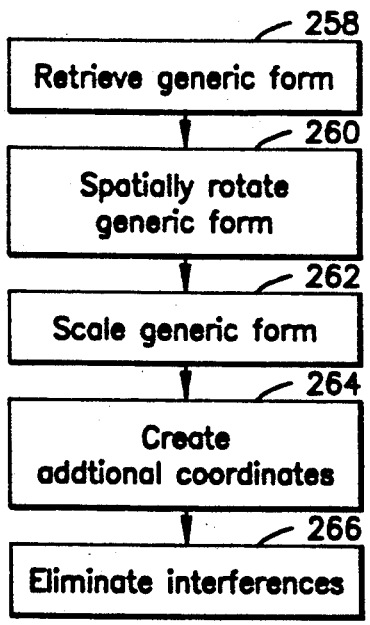
FIG. 23 is a flow chart describing a superimposition method in the second preferred embodiment.

FIG. 23 describes a method for superimposing the scanned coordinates onto a generic form stored in the database. Landmarks on the generic form are matched with, and compared to, corresponding landmarks on the scanned object, thereby providing a correct orientation and size for the generic form. The CAD/CAM software retrieves a generic form from the database (258). The generic form is "spatially rotated" and positioned so that it corresponds to a spatial orientation of the set of coordinates scanned from the object (260). This orientation is performed by matching at least three landmarks on the generic form with corresponding landmarks on the scanned object. The CAD/CAM software also scales the generic coordinates so they are sized substantially the same as the scanned coordinates (262). Additional coordinates are created to emphasize features of the object or generic form (264). Interferences among objects are eliminated (266).

Figure 24:
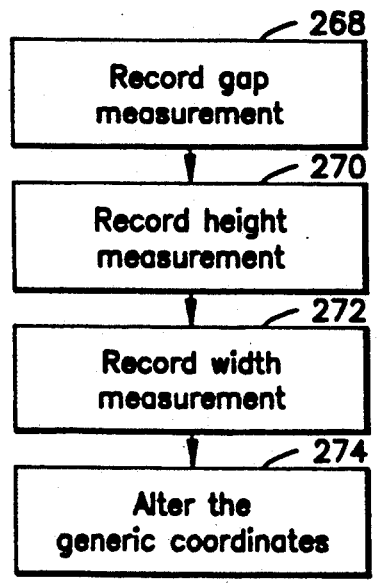
FIG. 24 is a flow chart describing a method for scaling coordinates in the second preferred embodiment.

FIG. 24 describes the scaling operation performed on the generic form. Gap measurements are recorded between the object and other objects adjacent to it (268). Also recorded are height and width measurements of the object and/or adjacent objects (270,272). The ratio of these values to the equivalent distances on the generic form yields a scaling factor. This scaling factor may be applied to the set of coordinates (274). Thus, the generic form can be sized to fit the space available for the reproduction. Note that with this method, a replacement part may be created using the computer-based generic form scaled according to the "gap" left for its placement, and from measurements of adjacent objects. Thus, the original object is not required when machining replacement parts, unless it is desired to construct a true, substantially identical "reproduction" of the object.

Figure 25:
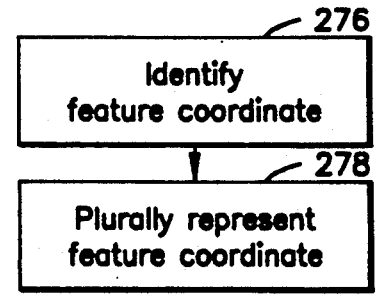
FIG. 25 is a flow chart describing a method of emphasizing features in the second preferred embodiment.

FIG. 25 describes a method for creating additional feature coordinates in the second preferred embodiment. Additional coordinates can be added to the set of coordinates to emphasize features of the object or the generic form. The additional coordinates ensure that the feature is not smoothed out, or otherwise eliminated, either by system operators or by the CAD/CAM software. A feature coordinate is identified within the set of coordinates (276). The CAD/CAM software plurally represents the feature coordinate by computing a plurality of parametric curves extending through the feature coordinate (278). These parametric curves are used to provide additional coordinates, thereby preventing the feature from being smoothed out or eliminated.

When the second preferred embodiment is used to produce dental prostheses, it incorporates information from both the scanned tooth and from the generic tooth form, like the first preferred embodiment. FIG. 12 illustrates this incorporation. A generic tooth form 136 stored in the database contains a local coordinate system 140, based on maximum height (in the occlusal plane) of the cusp tips. The database also contains the positions of the proximal contacts 142 and 144 relative to that local coordinate system 140. If a landmark 146 is placed on the prepared tooth 148, a local coordinate system 150 relative to the prepared tooth 148 can be calculated. Since the two contact points 142 and 144 on the prosthesis must match the two contact points on the proximal teeth, a transformation from the generic coordinates to the prosthesis coordinates can be made. With this transformation, a scaled generic form 136 is created for the prepared tooth configuration 148.

The design of the surfaces of the prosthesis is more complicated than simply transforming the coordinate system. The occlusal surface of the prosthesis is suggested by the generic tooth form stored in the database. However, as illustrated by FIGS. 13A and 13B, the prosthesis must contact the adjacent teeth 152 and 154. To accomplish this, the CAD/CAM software scales the generic tooth form so that the mesial-distal distance between proximal teeth matches the distance between contact points of the generic form. The scaling factor used is simply the ratio of actual mesial-distal length over the mesial-distal length of the generic form. Thus, the size of the generic form can be altered by checking the gap between the adjacent teeth 152 and 154. The width and height of the generic form can be determined by measuring the thickness and height of the adjacent teeth 152 and 154. Also, the coordinates representing the fossae and cusps of the occlusal surface may be altered to raise or lower the cusps. This scaling factor is most likely provided by measuring the upper and lower teeth while in occlusion.

FIGS. 14A and 14B show that the interference between the upper and lower teeth can be checked by using contour lines. Interferences are solved by moving the coordinates involved. The occlusal surface of the prosthesis 156 is checked when the teeth of the mandible and maxilla are in contact. First, the relative positions between mandible and maxilla teeth have to be found. FIG. 15 illustrates the data collection method. Impressions 160 in a wax plate 162 are digitized to find the relative position between the mandible and maxilla teeth. Landmarks 164 are plugged into the impression 160. The mandible and maxilla teeth can be digitized from opposite sides of the impression 160. Also, the positions of the landmarks 164 are digitized. Thus, the relative position of the mandible and maxilla teeth can be calculated based on the position of the landmarks 164.

As described by FIG. 12, the lower part of the prosthesis 134 fits over the prepared tooth. This prepared tooth surface 134 must be connected to the generic form providing the occlusal surface 136. Typically, a ruled surface 138 (e.g., straight, ruled lines) is generated from the margin of the prepared tooth surface to the parting line of the prosthesis. The resulting margin of the prosthesis is usually sharp. A small error near the edge could cause severe problems, such as too loose or too tight a fit.

THREE DIMENSIONAL REPRESENTATION

Figure 26:
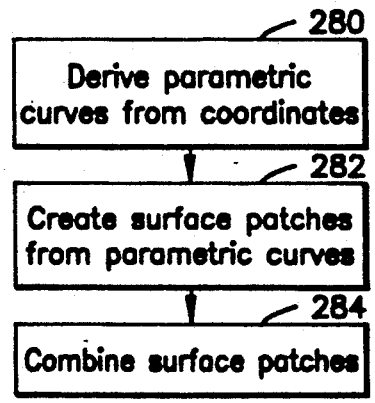
FIG. 26 is a flow chart describing a method for generating surface patches in the second preferred embodiment.

FIG. 26 describes a method for computing surface patches from the scanned coordinates in the second preferred embodiment. A plurality of parametric curves are derived from the coordinates (280). The surface patches are created from the parametric curves (282). The combined surface patches provide a three dimensional representation of the object (284).

The surface patches are defined by bi-cubic uniform B-splines with multiple knots for boundaries. B-splines are used for a number of reasons: (1) the surface can be changed locally by simply moving control vertices; (2) the control vertices approximate the interpolated surface; and (3) the surface can be constructed with simple equations. In addition, the B-spline geometry ensures continuity across the surface of the object without sudden changes to second order derivatives. This property ensures aesthetics and simplifies subsequent machining.

When the second preferred embodiment is used to produce dental prostheses, it is important that the prostheses surfaces are smooth and continuous. All external surfaces can be polished with round burrs because they are blended surfaces. Thus, there are no sharp points on the surface. These aesthetics are preserved with the use of B-splines. When machining begins, it is important to avoid sudden accelerations. Otherwise, damaged or broken tools result, and the workpiece materials may be gouged or torn. By ensuring continuity across the surface patches to second order derivatives, these problems can be eliminated.

PARTING LINE GENERATION

Figure 27:
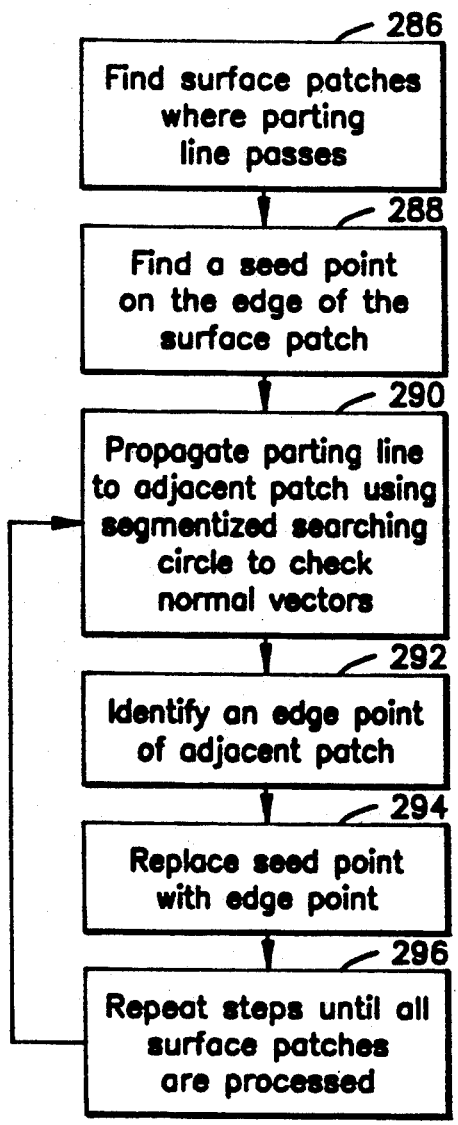
FIG. 27 is a flow chart describing a method for generating parting lines in the second preferred embodiment.

FIG. 27 describes a method for generating parting lines in the second preferred embodiment. Parting line generation occurs in the second preferred embodiment after the surface patches have been constructed. This allows the surface patches to be divided into regions by a parting line, so that undercuts and their associated interferences are avoided. The parting line on a surface patch is perpendicular to the cross-product of two vectors. The first vector is parallel to a first axis of the machine tool (the vertical Z-axis of a 3-axis milling machine). The second vector is a normal vector of a point on a surface patch.

The CAD/CAM software finds those surface patches through which the parting line passes (286). An edge of these surface patches has end points with different signs of surface normal component values parallel to an axis of the machine tool. A seed point is found on the edge (boundary) of a marked surface patch at which the component of the surface normal vector parallel to the machine tool axis equals zero (288). The seed point on the edge of the surface patch can be found, for example, by successively bisecting the edge until the surface normal component is zero. The parting line is propagated using a segmentized searching circle until an edge of an adjacent surface patch is encountered (290). An edge point of the adjacent surface patch is identified (292) and the seed point is replaced (294). These steps are repeated (i.e., the propagating step (290) through the replacing step (294)) until all found surface patches are processed (296).

As illustrated in FIG. 12, a single parting line in the second preferred embodiment typically defines two major regions for a dental prosthesis. One part of the configuration is a generic form 136 representing the occlusal surface and sides of the prosthesis to the crests of convexity (the two maximum horizontal points in any given radial scan line to the parting line). The generic form 136 is altered to fit the space available in the patient's mouth. The prepared tooth surface 148 determines the other part of the configuration. The lower part of the prosthesis 134 is manipulated to fit over the prepared tooth 148. Also included in this region is a connecting surface 138 between the generic form and the prepared tooth surface, i.e., the surface below the crest of convexity, typically extending from the parting line to the margin of the prosthesis.

SEGMENTIZED SEARCHING CIRCLE

Figure 28:
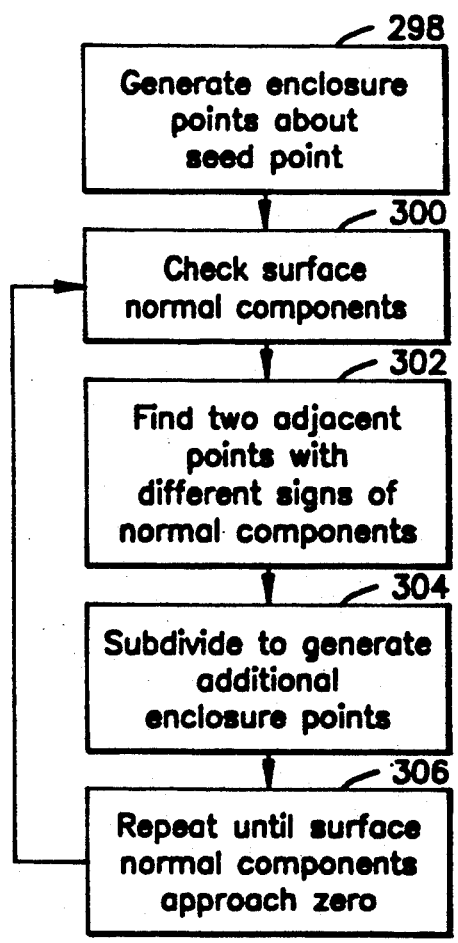
FIG. 28 is a flow chart describing a method for propagating segmented searching circles in the second preferred embodiment.

FIG. 28 describes a searching circle method of propagating lines through surface patches. The segmentized searching circle is propagated by first generating a plurality of enclosing points to create a substantially polygonal representation about a seed point (298). A plurality of line segments are derived between the enclosing points to enclose the seed point. The points are checked (300) to find two adjacent points which have different signs of surface normal components parallel to the machine tool axis (302). A new plurality of points with finer spacing are generated between the two points and the process repeats until the desired accuracy is obtained (304). These steps are repeated (i.e., the checking step (300) through the generating step (304)) until an edge of an adjacent surface patch is encountered (306).

Figure 29:
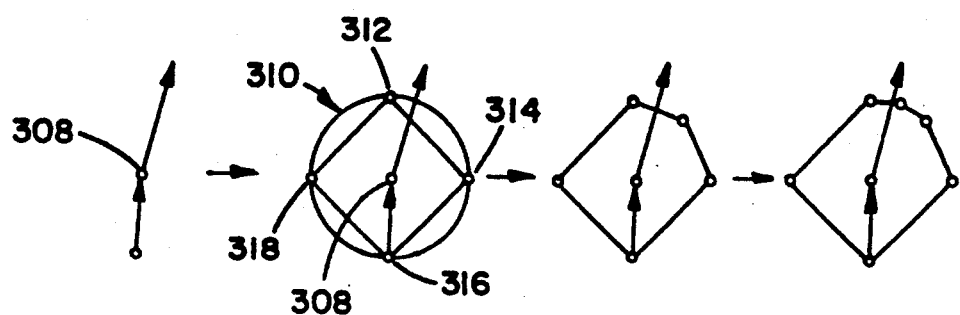
FIG. 29 illustrates the segmented searching circle method.

FIG. 29 illustrates the segmented searching circle algorithm. A segmentized searching circle is a modification of the bisection algorithm. If any continuum is being searched for points having a particular value and a seed point 308 is known which has that value, an adjacent point having that value can be located by drawing a circle 310 about the seed point 308 and evaluating points 312 314, 316, and 318 on the circumference of that circle 310. Instead of evaluating all points on the circumference, only the selected points 312, 314, 316, and 318 are evaluated to locate a segment that contains the desired value. The segment is successively subdivided until a point equal to or sufficiently close to the desired value is located. Subdivision is accomplished by mathematically rotating the search vector.

As shown in FIG. 29, when this method is applied to searching, the seed point 308 must be found first. At the first stage of searching, four points 312, 314, 316, and 318, on the circle 310 are evaluated and each segment between two points is checked for the given value. If a segment is found, it will be subdivided until the given tolerance or cut-off criterion is reached. In the process, the searching radius can be changed if necessary. Note that for successive steps, the point found at the given radius becomes the new seed point and the old seed point 308 is used as the first point on the search circle.

Figure 30:
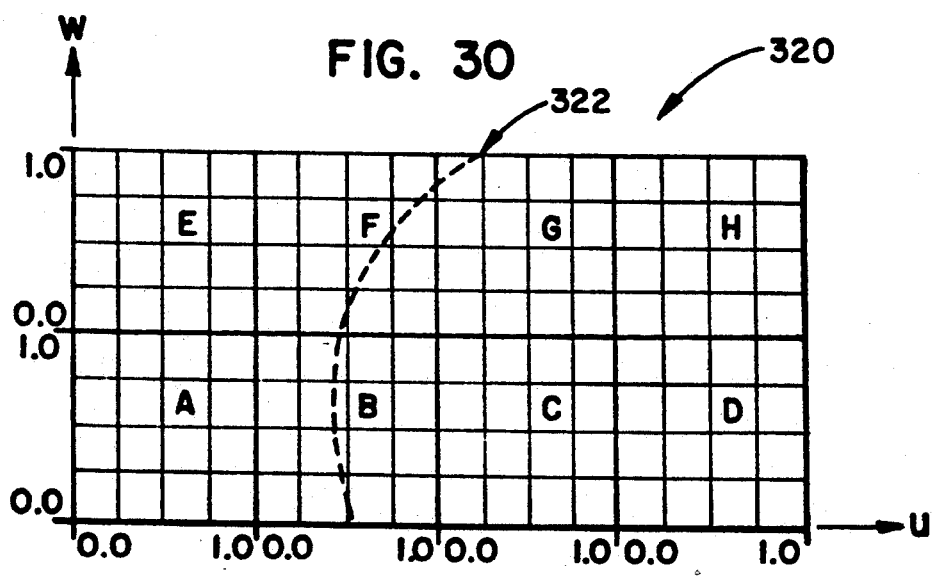
FIG. 30 illustrates a surface composed of eight surface patches in a parametric domain.
Figure 31:
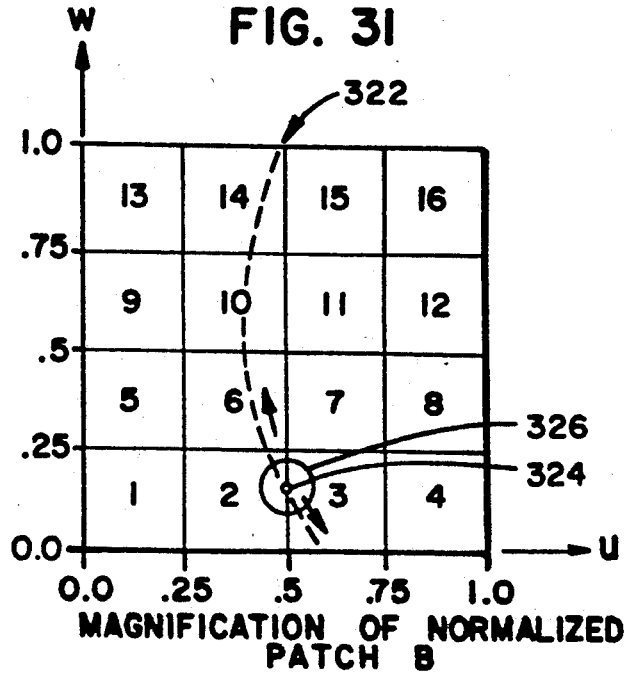
FIG. 31 illustrates the propagation of a searching circle on a single surface patch in the parametric domain.

FIG. 30 shows a surface 320 as defined by 4×2 normalized parametric patches A-H. A surface S(x,y,z), in cartesian coordinates, is the mapping of a surface P(u,w), in the parametric domain, wherein P(u,w) is the equation of a uniform bi-cubic B-spline surface. Each patch A-H has 4×4 subpatches. A curve 322 passes through normalized parametric patches B, F and G. FIG. 31 is a magnification of region B. Initially, a seed point 324 must be found, using any convenient method such as a bisection algorithm. If a seed point 324 is found between subpatch 2 and 3, there are two intersection points between the curve 322 and the searching circle 326. If subpatch 3 is selected for processing, the edge between 2 and 3 is marked. Subpatch 3 is selected by examining normal vectors. The center of the searching circle 326 is updated by moving it to the point most recently located on the curve 322. If the searching circle 326 meets the boundary of the normalized parametric patch B, subpatch 3 is marked as processed and the center of the searching circle 326 moves to the point in subpatch 2 which was found earlier. Then, subpatch 2 is processed. When the searching circle 326 passes the edge between subpatch 2 and 6, subpatch 2 is marked as processed. If the searching circle 326 meets the boundary of normalized parametric patch B, the seed point on the boundary of normalized parametric patch F is computed from calculations based on the normal vector. This sequence continues until all patches are processed.

CONTOURING

Figure 32:
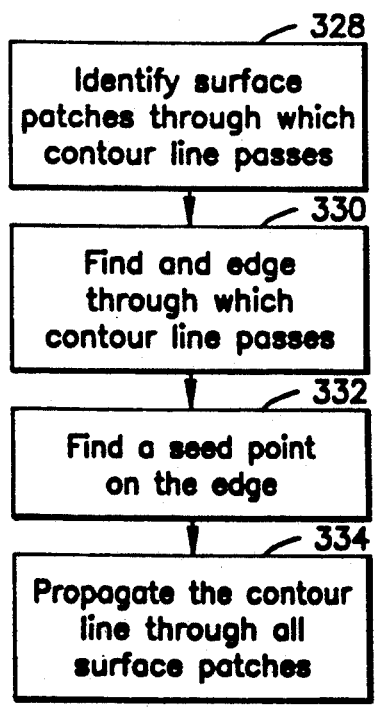
FIG. 32 describes a method for generating contour lines in the second preferred embodiment.

FIG. 32 describes a method for contouring surface patches in the second preferred embodiment. Contouring involves finding an intersection curve between a surface patch and a contour plane. The surface patches are contoured to provide a plurality of offset tool paths for the machine tool. The CAD/CAM software first identifies all surface patches through which a contour line passes (328). An edge of the identified surface patch is found (330). A seed point is selected on the edge (332). The seed point may be found, for example, by bisecting the edge. The contour line is propagated from the seed point using a segmentized searching circle until it processes all of the identified surface patches (334).

Figure 33:
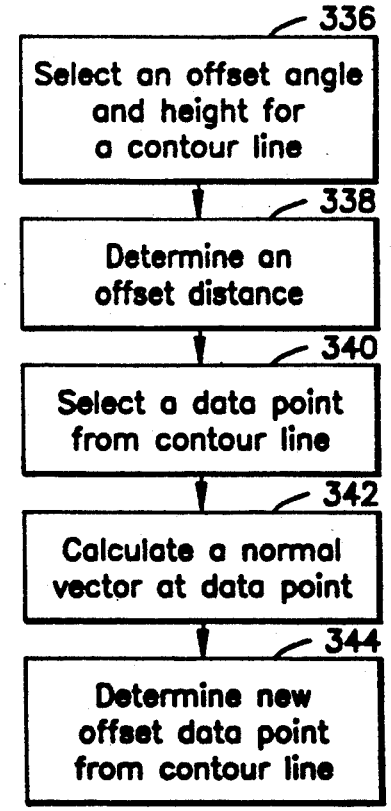
FIG. 33 describes a method for generating offset tool paths in the second preferred embodiment.

FIG. 33 describes a method for creating offset tool paths in the second preferred embodiment. Offsets can be applied to regions automatically selected by the CAD/CAM software. Alternatively, offsets can be applied to regions manually selected by an operator. The CAD/CAM software selects an offset angle and an offset height from the contour line (336). The offset angle and the offset height determine the offset distance (338). A data point is projected from the contour line onto a plane to simplify normal vector calculation (340). A normal vector is calculated at this data point (342). A new offset data point is determined by shifting the data point offset a distance along the normal vector (344).

TOOL INTERFERENCE CHECK

Figure 34:
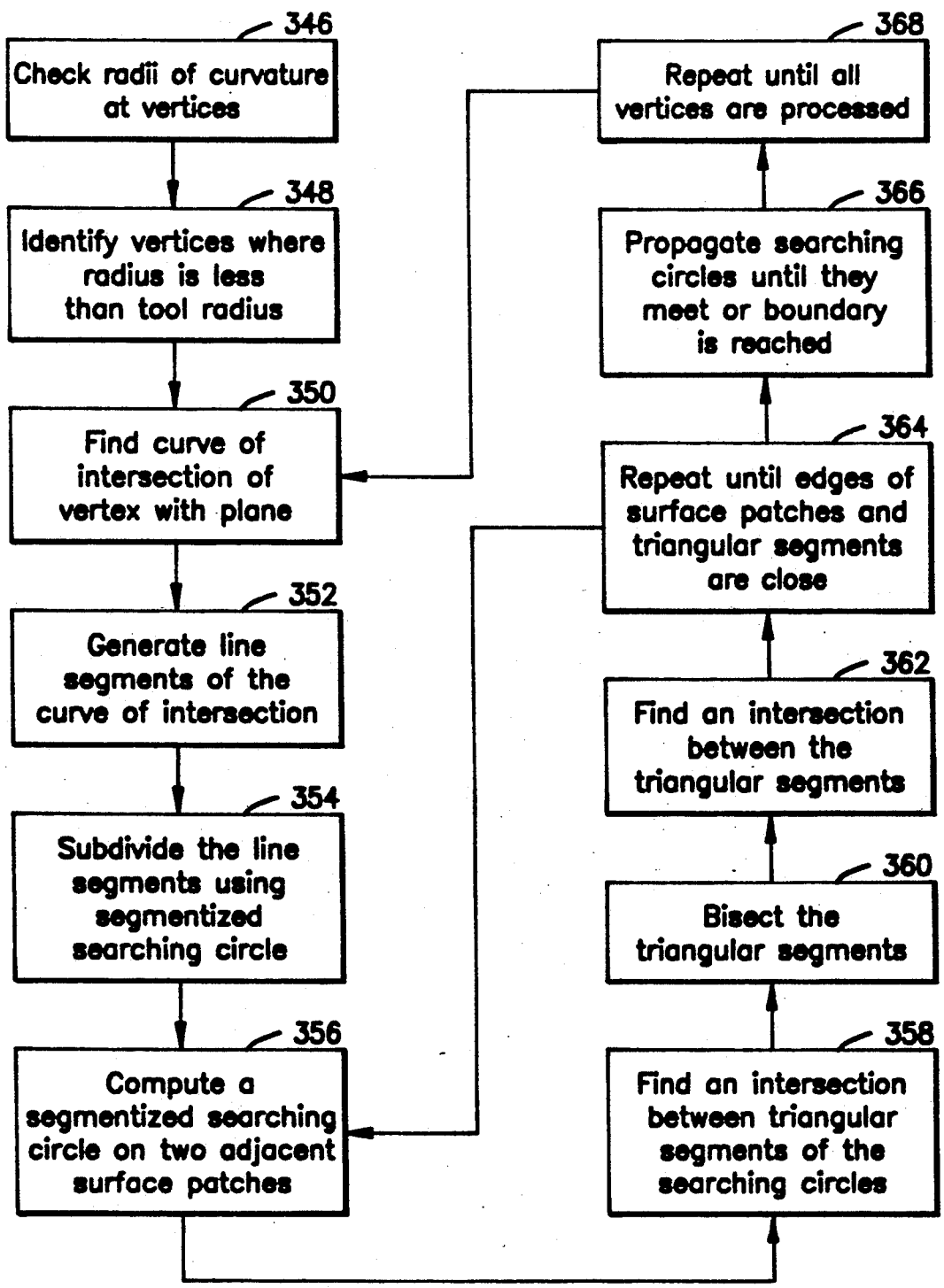
FIG. 34 describes a method for eliminating tool interferences in the second preferred embodiment.

FIG. 34 describes a method for preventing tool interference in the second preferred embodiment. The method prevents the machine tool from erroneously intersecting with one of the surface patches. The CAD/CAM software checks the minimum radii of principal curvature at a plurality of vertices of the surface patches (346). The vertices where the minimum radius is smaller than the tool radius are identified (348). The CAD/CAM software finds a curve of intersection of each identified vertex with a plane. The plane passes through the identified vertex and contains a first vector normal to the offset patch and a second vector in the direction of the minimum radius (350). A plurality of line segments of the intersection curve are generated, which line segments intersect together (352). The line segments are subdivided using a segmentized searching circle, until an error value between the line segments and the surface patch approaches a predetermined tolerance value (354). A segmentized searching is computed circle for the two adjacent surface patches (356). An intersection between a plurality of triangular segments of the segmentized searching circles is found (358). The triangular segments are bisected (360). An intersection between the triangular segments is formed (362). These steps are repeated (i.e., the segmentized searching circle computing step (356) through the intersection finding step (362)) until an error value between a plurality of intersected edges of the triangular segments and the surface patches approaches the predetermined tolerance (364). The segmentized searching circles are propagated until the circles meet or until the circles reach one of a plurality of boundaries for the surface patches (366). These steps are repeated (i.e., the curve of intersection finding step (350) through the segmentized searching circle propagating step (366)) until all identified vertices are processed (368).

MACHINE TOOL OPTIMIZATION

Figure 35:
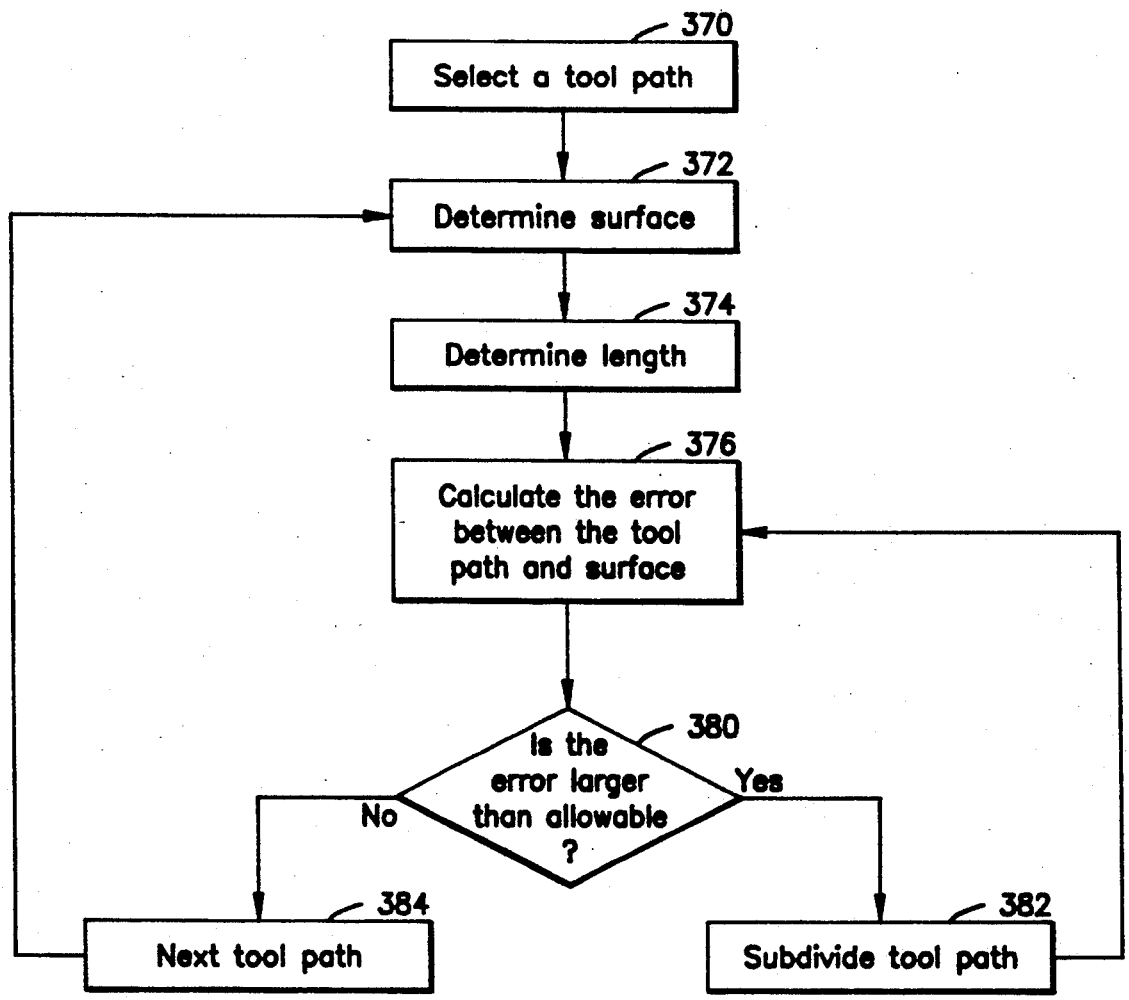
FIG. 35 describes a method for optimizing step lengths in both preferred embodiments.
Figure 36:
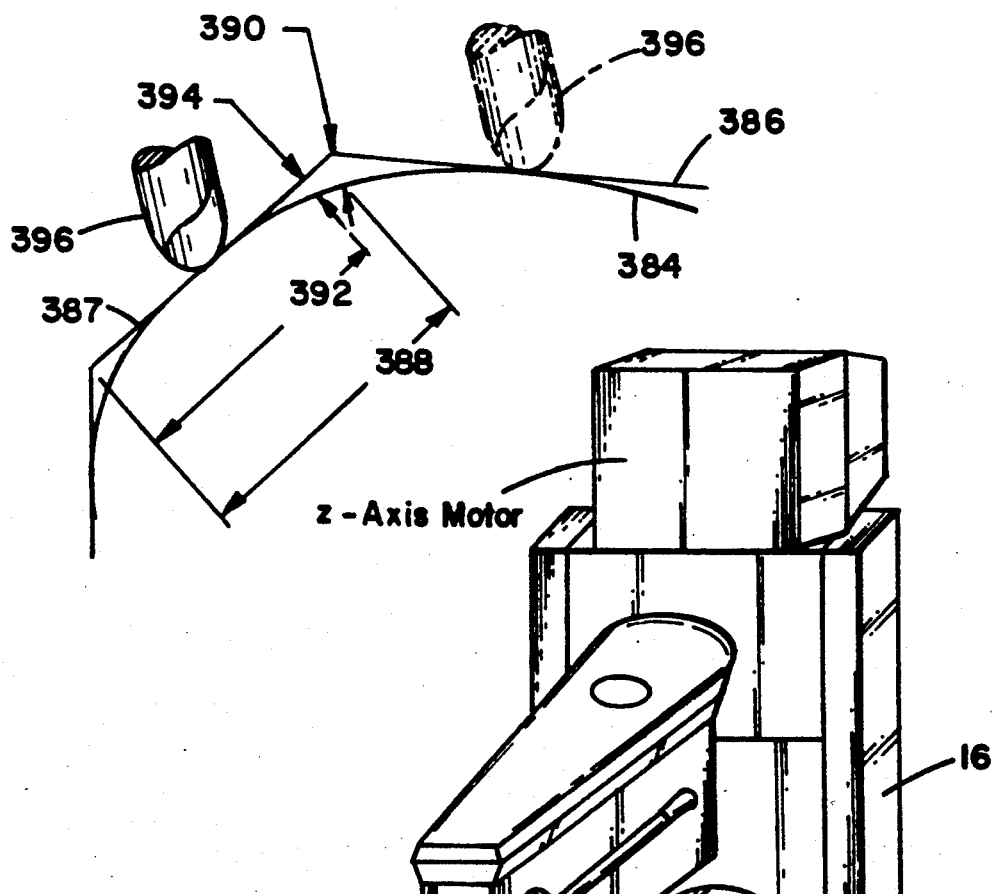
FIG. 36 illustrates the optimization of tool path step lengths in both preferred embodiments.

FIG. 35 describes a method for optimizing offset tool paths in both preferred embodiments. FIG. 36 illustrates offset tool paths 386 and 387. The CAD/CAM software can optimize the step length of the cutter 396 along the tool paths 386 and 387 (370). Since the desired surface 384 is known (372), along with a possible tool path 387 of length 388 (374), the maximum error 390 can be obtained (376). If the maximum error 390 is larger than an allowable value (380), the tool path length 388 is subdivided (382) until the calculated error 394 is less than an allowable value (384). The reduction in tool path step length 392 is determined by the known surface 384 and the allowable value for the calculated error 394.

Figure 37:
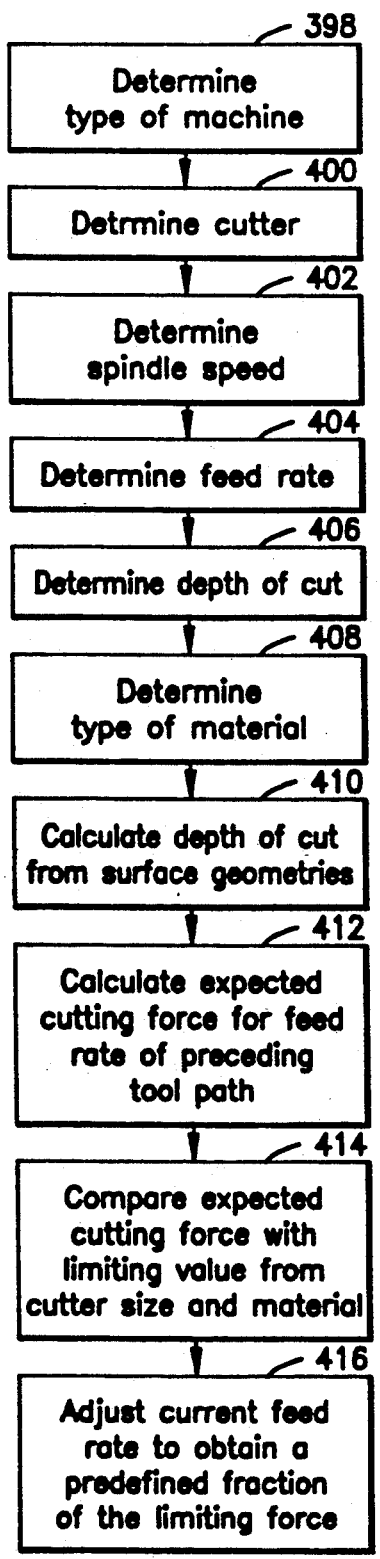
FIG. 37 describes a method for optimizing cutter feed rates in both preferred embodiments.

FIG. 37 describes a method for optimizing the cutter feed rate in both preferred embodiments. Based on the characteristics of the machine tool (398), the cutter (400), a spindle speed (402), a feed rate (404), a depth of cut (406), and the type of material machined (408), the depth of cut is calculated from known surface geometries (410). An expected cutting force is calculated for the feed rate in the immediately preceding tool path increment (412). This expected force is compared with a limiting value of force based on cutter size and material (414). Feed rate in the current tool movement increment is adjusted to produce an estimated cutting force of a predefined fraction of the limiting force value (416).

Figure 38:
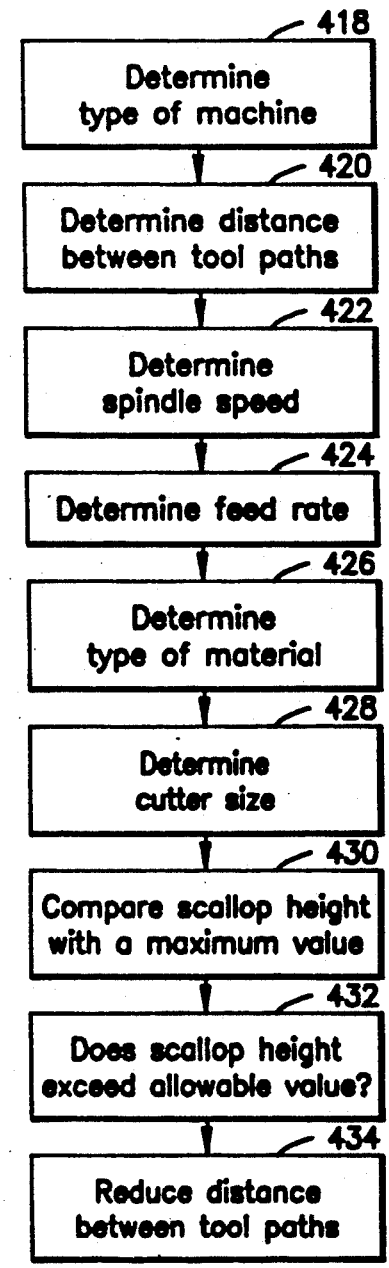
FIG. 38 describes a method for optimizing scallop heights in both preferred embodiments.

FIG. 38 describes a method for optimizing scallop heights in both preferred embodiment. FIG. 39 graphically illustrates the optimization of the scallop height. The machining parameters include the characteristics of the tool path (418), the distance between tool paths (420), the spindle speed (422), the feed rate (424), the characteristics of the material (426), and the size of the cutter 446 (428). The scallop height 436 is compared with a predetermined maximum value (430), and if the scallop height 436 exceeds the predetermined maximum value (432), the distance between adjacent tool paths 438 is reduced and the offset tool paths are adjusted (434). The distance 438 is specific to the cutter geometry and machined surface profile, particularly the cutter radius 440 and surface curvature 442.

FIXTURING

Figure 40:
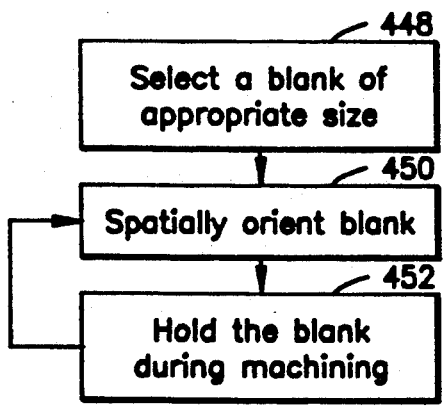
FIG. 40 describes a method for fixturing workpiece materials in both preferred embodiments.

FIG. 40 describes a method for fixturing in both preferred embodiments. A blank of the workpiece material, of appropriate size, is chosen (448). The blank is oriented according to the spatial orientation of the set of coordinates (450). The workpiece material is held on a bed surface of the machine tool to prevent movement while the machine tool operates (452).

The blank also may be selected from a plurality of rough cut, preformed blanks. These preformed blanks, which correspond to generic forms stored in the database, eliminate the need for multiple machining passes for each region. The correct blanks preformed blanks are selected by the CAD/CAM software.

A modified vise may be attached to the bed of the machine tool to hold the blank. A special fixture is milled, representing the configuration of where the reproduction is to fit. When used to produce dental prostheses, this configuration represents the prepared tooth (similar to a die in the wax casting technique). The internal surface and the external surface of the reproduction are milled to the heights of contour from another blank. The partially fabricated reproduction is removed from the vise and placed onto the fixture. When used to produce dental prostheses, this preserves the relative orientation between the internal and external surfaces when the final occlusal surface is machined. The partially fabricated reproduction is held in place with either sticky wax or epoxy. The fixture is held with the vise while the remaining portion of the external surface is cut. The fixture can also serve as a holding device and can be used during shipping as protection for the margins. This protection is probably not critical for metal reproductions, but may very practical for ceramic reproductions which are brittle and more susceptible to fracture and cracking.

Alternatively, as described hereinbefore, one or more parting lines can divide the three dimensional representation of the object into top and bottom portions. The bottom portion is machined first. The object is then flipped and the bottom portion is secured onto the fixture. Finally, the top portion is machined, completing the reproduction.

MACHINING

Figure 41:
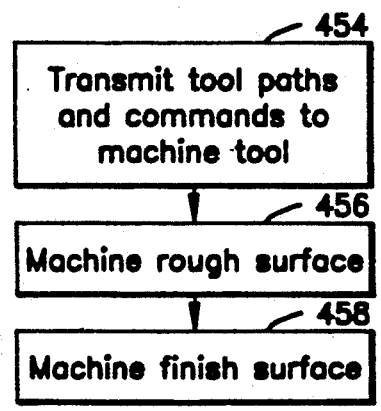
FIG. 41 describes a method for machining workpiece materials in both preferred embodiments.

FIG. 41 describes a method of machining used in both preferred embodiments. The machining operation begins with the transmittal of the tool paths and commands from the CAD/CAM software to the machine tool (454). The machine tool machines both rough and finish surfaces as transmitted (456,458). The tool paths are transmitted by region, so that the machine tool, may if desired, machine a blank by region according to the tool paths received.

FIGS. 42A, 42B, 42C, and 43 illustrate the machining process. The surface of the raw stock or blank 460 and the offset 464 of the part surface 466 are the geometrical constraints that determine the tool paths for the rough (if required) and finish cutting. The offset value 464 is determined by the tool radius plus the material left for finish cutting. Rough cutting is the process of removing the bulk of the material 462 from the raw stock 460, using the full capability of the machine tool. The factors related to roughing are the available spindle power, tools, and material properties. The tool path for roughing depends on the shape of the raw stock 460 and the offset surface 464.

The cutting plane 468 moves down according to the maximum cutting depth along the Z axis. For each cutting plane 468, the intersection lines between the raw stock 460 and the offset surface 464 have to be calculated to determine the roughing area 462. The roughing area 462 can be removed by contour cutting. Starting at a tool path that produces the desired contour, the machining continues outward until all rough cutting material is removed. If the machine tool meets the offset surface 464, it is retracted, moved to a position above the next rough cutting tool path and lowered to the cutting plane 468 to continue the rough cutting. The process repeats until all the rough cutting area 462 is removed.

The availability of detailed descriptions of the reproduction to be machined in numerical format enables different cutting paths other than contour cutting paths to be easily generated. Numerical procedures can be used to produce any sequence of points on the surface and hence any desired cutting tool path between points on the surface. Particular applications are cutting tool paths which directly follow the part scanning paths, i.e., radial tool paths that eliminate computation steps, spiral tool paths, and raster tool paths. In spiral cutting, tool movement is around the vertical axis of the blank held on the tool bed. If the radial tool position is incremented for each tool movement step, an approximately spiral tool path results.

Finish cutting, as shown in FIG. 43, removes the small amount of excess material left during the roughing process, thus bringing the surface of the reproduced object 72 to the required geometry and surface finish. Usually, in finish cutting, the feed rate is low and spindle speed high. The tool path for the finish cutting is determined by finding the intersection lines between the offset surface and the X-Z plane in FIG. 42A. Polishing is the final process of eliminating all machining marks and shining the surface. This process can be done by using a rotating brush, grinding tool, or it can be performed manually.

Figure 44:
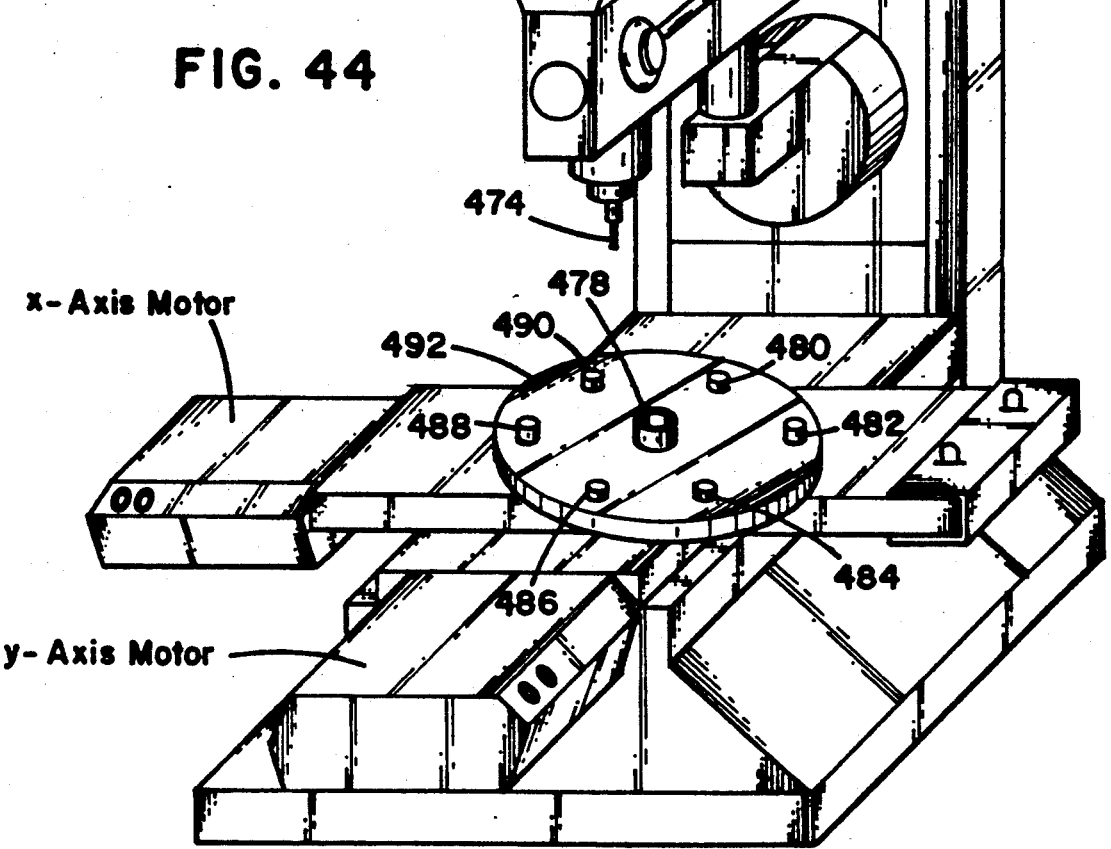
FIG. 44 illustrates a three axis machine tool used with both preferred embodiments.

FIG. 44 illustrates both one possible fixturing method and a three axis machine tool. A blank workpiece of appropriate size is chosen and placed in the adaptable fixture 478. The holder 478 secures the workpiece in place. A region of the workpiece is machined using the cutting tool 474. The workpiece is removed from the fixture 478 and re-oriented. The workpiece may also be secured in different size fixtures 480-490.

Although two embodiments have been illustrated and described herein, it will be appreciated by those of ordinary skill in the art that any arrangement which is calculated to achieve the same purpose may be substituted for the specific embodiments shown. This application is intended to cover any adaptations or variations of the present invention. Therefore, it is manifestly intended that this invention be limited only by the claims and equivalence thereof.

APPENDIX

Hereby incorporated by reference for the purpose of providing demonstrative evidence of the level of skill in the art are the following citations:

B-Splines and Inverse Algorithms:
D. H. Ballard and C. M. Brown, *Computer Vision*, Prentice-Hall, Inc., 1982, p. 239-243.
    D. F. Rogers and J. A. Adams, *Mathematical Elements for Computer Graphics*, Prentice-Hall, Inc., 1976, p. 144-155.
    P. Lancaster and K. Salkauskas, *Curve and Surface Fitting*, Academic Press, 1986, p. 87-112.
    S. Peterson, X. Zhu, and D. Riley, *A New Algorithm for Constructing B-Spline Surfaces*, Computers in Engineering 1984, Vol. 3, Proceedings of the ASME Third International Computers in Engineering Conference, Chicago, Illinois, August 1984, p. 137-144

Surface Patches:
    D. F. Rogers and J. A. Adams, *Mathematical Elements for Computer Graphics*, McGraw-Hill, 1976, p. 157-187.
    P. Lancaster and K. Salkauskas, *Curve and Surface Fitting*, Academic Press, 1986, p. 245-271.

Linear Transformations:
    D. F. Rogers and J. A. Adams, *Mathematical Elements for Computer Graphics*, McGraw-Hill, 1976, p. 5.
    D. H. Ballard and C. M. Brown, *Computer Vision*, Prentice-Hall, Inc. 1982, p. 473.

What is claimed is:

1. A method of machining a reproduction of a 3-dimensional object such that the reproduction substantially duplicates all surfaces of said object, comprising:
   (a) retrieving at least one generic form of said object from a computer, said generic form comprised of at least one set of coordinates residing on a plurality of scan lines;
   (b) using a computer, automatically identifying feature coordinates in said set of coordinates to emphasize features on said generic form;
   (c) generating a plurality of parametric curves extending through said feature coordinates;
   (d) generating a parting line through said scan lines to divide said generic form into a plurality of regions to avoid undercuts and associated interferences during machining;
   (e) generating a plurality of contour lines between coordinates on adjacent said scan lines, said coordinates including said feature coordinates;
   (f) fixturing a material to be shaped into the reproduction of said object such that said material may be machined; and
   (g) transmitting a plurality of tool paths computed from said contour lines from the computer to a machine tool such that said machine tool is directed to machine the reproduction of said object.

2. The method of claim 1, further comprising generating at least one parting line in the computer such that said coordinates below said parting line are clipped from said scan lines.

3. The method of claim 1, further comprising connecting said sets of coordinates at a common edge, when said common edge exists.

4. The method of claim 3, further comprising selectively offsetting said contour lines in the computer, thereby providing a predetermined offset from a surface of said object for said tool paths.

5. The method of claim 1, further comprising preventing said tool paths from erroneously intersecting with said surface.

6. The method of claim 1, further comprising generating at least one command directing said machine tool to machine a material into the reproduction of said first object to within a predetermined tolerance.

7. A method of machining a reproduction of a 3-dimensional object such that the reproduction substantially duplicates all surfaces of said object, comprising:
   (a) scanning said object and recording into a computer at least one set of coordinates defining a plurality of scan lines;
   (b) using a computer, automatically identifying feature coordinates in said set of coordinates to emphasize features on said object;
   (c) generating a plurality of parametric curves extending through said feature coordinates;
   (d) generating a parting line through said scan lines to divide said object into a plurality of regions to avoid undercuts and associated interferences during machining;
   (e) generating a plurality of contour lines between coordinates on adjacent said scan lines, said coordinates including said feature coordinates;
   (f) fixturing a material to be shaped into the reproduction of said object such that said material may be machined sequentially by a machine tool through alternate orientation of said material in accordance with said regions; and
   (g) transmitting a plurality tool paths computed from said contour lines from the computer to said machine tool such that said machine tool is directed to machine the reproduction of said object.

8. The method of claim 7, further comprising generating at least one parting line in the computer such that said coordinates below said parting line are clipped from said scan lines.

9. The method of claim 7, further comprising superimposing said set of coordinates onto at least one generic form of said object in the computer thereby creating at least one altered generic set of coordinates.

10. The method of claim 7, further comprising connecting said sets of coordinates at a common edge, when said common edge exists.

11. The method of claim 7, further comprising selectively offsetting said contour lines in the computer, thereby providing a predetermined offset from said surface for said tool paths.

12. The method of claim 7, further comprising preventing said tool paths from erroneously intersecting with one said surface.

13. An apparatus for machining a reproduction of a 3-dimensional object such that the reproduction substantially duplicates all surfaces of said object, comprising:
   (a) at least one computer;

(b) means for retrieving at least one generic form of said object from the computer, said generic form comprised of at least one set of coordinates residing on a plurality of scan lines;

(c) means for automatically identifying feature coordinates in said set of coordinates to emphasize features on said generic form;

(d) means for generating a plurality of parametric curves extending through said feature coordinates;

(e) means for generating a parting line through said scan lines in the computer to divide said generic form into a plurality of regions to avoid undercuts and associated interferences during machining;

(f) means for generating a plurality of contour lines between coordinates on adjacent said scan lines, said coordinates including said feature coordinates;

(g) means for fixturing a material to be shaped into the reproduction of said object such that said material may be machined; and (g) means for transmitting a plurality of tool paths computed from said contour lines from the computer to a machine tool such that said machine tool is directed to machine the reproduction of said object.

14. The method of claim 13, further comprising means for generating at least one parting line in the computer such that said set of coordinates are clipped from said scan lines below said parting line.

15. The method of claim 13, further comprising means for connecting said sets of coordinates at a common edge.

16. The method of claim 13, further comprising means for selectively offsetting said contour lines in the computer, thereby providing a predetermined offset from said surface for said tool paths.

17. The method of claim 13, further comprising means for preventing said tool paths from erroneously intersecting with said surface.

18. The method of claim 13, further comprising means for generating at least one command directing said machine tool to machine a material into the reproduction of said first object to within a predetermined tolerance.

19. An apparatus for machining a reproduction of a 3-dimensional object such that the reproduction substantially duplicates all surfaces of said object, comprising:

(a) at least one computer;

(b) at least one machine tool operatively connected to said computer;

(c) means for scanning said object and recording into the computer at least one set of coordinates defining a plurality of scan lines;

(d) means for automatically identifying feature coordinates in said set of coordinates to emphasize features on said object;

(e) means for generating a plurality of parametric curves extending through said feature coordinates;

(f) means for generating a parting line through said scan lines int he computer to divide said object into a plurality of regions to avoid undercuts and associated interferences during machining;

(g) means for generating a plurality of contour lines between coordinates on adjacent said scan lines, said coordinates including said feature coordinates;

(h) means for fixturing a material to be shaped into the reproduction of said object such that said material may be machined sequentially by said machine tool through alternate orientation of said material in accordance with said regions; and (i) means for transmitting a plurality of tool paths from the computer to said machine tool such that said machine tool is directed to machine the reproduction of said object.

20. The apparatus of claim 19, further comprising means for generating at least one parting line in the computer such that said coordinates are clipped from said scan lines below said parting line.

21. The apparatus of claim 19, further comprising means for superimposing said sets of coordinates in the computer onto at least one generic form of said object in the computer.

22. The apparatus of claim 19, further comprising means for connecting said sets of coordinates at a common edge, when said common edge exists.

23. The apparatus of claim 19, further comprising means for selectively offsetting said contour lines in the computer, thereby providing a predetermined offset from said surface for said tool paths.

24. The apparatus of claim 19, further comprising means for preventing said tool paths from erroneously intersecting with said surface.

25. A method of machining a reproduction of a 3-dimensional object such that the reproduction substantially duplicates all surfaces of said object, comprising:

(a) retrieving at least one generic form of said object from the computer, said generic form comprised of at least one set of coordinates;

(b) using a computer, automatically identifying feature coordinates in said set of coordinates to emphasize features on said generic form;

(c) generating a plurality of parametric curves extending through said feature coordinates;

(d) computing a plurality of surface patches in the computer from said set of coordinates, said coordinates including said feature coordinates;

(e) generating a parting line through said surface patches in the computer to divide said generic form into a plurality of regions to avoid undercuts and associated interferences during machining;

(f) fixturing a material to be shaped into the reproduction of said object such that said material may be machined; and (g) transmitting a plurality of tool paths computed from said surface patches from the computer to a machine tool such that said machine tool is directed to machine the reproduction of said object.

26. The method of claim 25, further comprising connecting said sets of coordinates at a common edge, when said common edge exists.

27. The method of claim 25, further comprising generating at least one parting line in the computer such that said set of coordinates is divided into a plurality of regions for sequential machining.

28. The method of claim 25, further comprising contouring said surface patches in the computer to provide a plurality of contour lines for said machine tool.

29. The method of claim 25, further comprising selectively altering said contour lines in the computer, thereby providing a predetermined offset from said surface patches for said machine tool.

30. The method of claim 25, wherein the computing step (b) further comprises computing said tool paths in the computer such that said machine tool is prevented from erroneously intersecting with one of said surface patches.

31. The method of claim 25, further comprising generating at least one command directing said machine tool to machine a material into the reproduction of said first object to within a predetermined tolerance.

32. A method of machining a reproduction of a 3-dimensional object such that the reproduction substantially duplicates all surfaces of said object, comprising:
(a) scanning said object and recording into a computer at least one set of coordinates;
(b) using a computer, automatically identifying feature coordinates in said set of coordinates to emphasize features on said object;
(c) generating a plurality of parametric curves extending through said feature coordinates;
(d) computing a plurality of surface patches in the computer from said set of coordinates, said coordinates including said feature coordinates;
(e) generating a parting line through said surface patches to divide said object into a plurality of regions in the computer to avoid undercuts and associated interferences during machining;
(e) fixturing a material to be shaped into the reproduction of said object such that said material may be machined sequentially by a machine tool through alternate orientation of said material; and
(f) transmitting a plurality tool paths corresponding to said surface patches from the computer to said machine tool such that said machine tool is directed to machine the reproduction of said object.

33. The method of claim 32, further comprising superimposing said sets of coordinates onto at least one generic form of said object in the computer such that said sets of coordinates are replaced with at least one altered generic set of coordinates.

34. The method of claim 32, further comprising connecting said sets of coordinates at a common edge, when said common edge exists.

35. The method of claim 32, further comprising generating at least one parting line in the computer such that said surface patches are divided into a plurality of regions.

36. The method of claim 32, further comprising contouring said surface patches in the computer to generate a plurality of contour lines for said machine tool.

37. The method of claim 36, further comprising selectively altering said contour lines in the computer, thereby providing a predetermined offset from said surface patches for said machine tool.

38. The method of claim 32, further comprising preventing said tool paths from erroneously intersecting with one of said surface patches.

39. An apparatus for machining a reproduction of a 3-dimensional object such that the reproduction substantially duplicates all surfaces of said object, comprising:
(a) at least one computer;
(b) means for retrieving at least one generic form of said object from the computer, said generic form comprised of at least one set of coordinates;
(c) means for automatically identifying feature coordinates in said set of coordinates to emphasize features on said generic form;
(d) means for generating a plurality of parametric curves extending through said feature coordinates;
(e) means for computing a plurality of surface patches in the computer from said set of coordinates, said coordinates including said feature coordinates;
(f) means for generating a parting line through said surface patches in the computer to divide said generic form into a plurality of regions to avoid undercuts and associated interferences during machining;
(g) means for fixturing a material to be shaped into the reproduction of said object such that said material may be machined; and
(h) means for transmitting a plurality of tool paths computed from said surface patches from the computer to a machine tool such that said machine tool is directed to machine the reproduction of said object.

40. The method of claim 39, further comprising means for connecting said sets of coordinates at a common edge, when said common edge exists.

41. The method of claim 39, further comprising means for generating at least one parting line in the computer such that said set of coordinates is divided into a plurality of regions for sequential machining.

42. The method of claim 39, further comprising means for contouring said surface patches in the computer to provide a plurality of contour lines for said machine tool.

43. The method of claim 42, further comprising means for selectively altering said contour liens in the computer, thereby providing a predetermined offset from said surface patches for said machine tool.

44. The method of claim 39, wherein the means for computing (c) further comprises means for preventing said tool paths from erroneously intersecting with one of said surface patches.

45. The method of claim 39, further comprising means for generating at least one command directing said machine tool to machine a material into the reproduction of said first object to within a predetermined tolerance.

46. An apparatus for machining a reproduction of a 3-dimensional object such that the reproduction substantially duplicates all surfaces of said object, comprising:
(a) at least one computer;
(b) at least one machine tool operatively connected to said computer;
(c) means for scanning said object and recording into the computer at least one set of coordinates;
(d) means for automatically identifying feature coordinates in said set of coordinates to emphasize features on said object;
(e) means for generating a plurality of parametric curves extending through said feature coordinates;
(f) means for computing a plurality of surface patches in the computer from said set of coordinates, said coordinates including said feature coordinates;
(g) means for generating a parting line through said surface patches in the computer to divide said object into a plurality of regions to avoid undercuts and associated interferences during machining;
(h) means for fixturing a material to be shaped into the reproduction of said object such that said material may be machined sequentially by said machine tool through alternate orientation of said material in accordance with said regions; and
(i) means for transmitting a plurality tool paths corresponding to said surface patches from the computer to said machine tool such that said machine tool is directed to machine the reproduction of said object.

47. The apparatus of claim 46, further comprising means for superimposing said sets of coordinates in the computer onto at least one generic form of said object in the computer such that said sets of coordinates are replaced with at least one altered generic act of coordinates.

48. The apparatus of claim 46, further comprising means for connecting said sets of coordinates at a common edge, when said common edge exists.

49. The apparatus of claim 46, further comprising means of generating at least one parting line in the computer such that said surface patches are divided into a plurality of regions.

50. The apparatus of claim 46, further comprising means for contouring said surface patches in the computer to generate a plurality of contour lines for said machine tool.

51. The apparatus of claim 50, further comprising means for selectively altering said contour lines in the computer, thereby providing a predetermined offset from said surface patches for said machine tool.

52. The apparatus of claim 46, further comprising means for computing said tool paths in the computer to prevent said machine tool from erroneously intersecting with one of said surface patches.

* * * * *